US007238479B2

(12) United States Patent
Smith et al.

(10) Patent No.: US 7,238,479 B2
(45) Date of Patent: Jul. 3, 2007

(54) **SINGLE NUCLEOTIDE POLYMORPHISM MARKERS IN THE BOVINE *CAPN1* GENE TO IDENTIFY MEAT TENDERNESS**

(75) Inventors: Timothy P. Smith, Hastings, NE (US); Eduardo Casas, Hastings, NE (US)

(73) Assignee: The United States of America as represented by the Secretary of Agriculture, Washington, DC (US)

( * ) Notice: Subject to any disclaimer, the term of this patent is extended or adjusted under 35 U.S.C. 154(b) by 369 days.

(21) Appl. No.: 10/739,904

(22) Filed: Dec. 18, 2003

(65) Prior Publication Data

US 2005/0181373 A1    Aug. 18, 2005

(51) Int. Cl.
*C12Q 1/58* (2006.01)
*C07H 21/04* (2006.01)
*C07H 21/02* (2006.01)
*C07K 14/435* (2006.01)
*G01N 33/53* (2006.01)

(52) U.S. Cl. .................... 435/6; 435/7.1; 536/23.5; 536/24.31; 530/350

(58) Field of Classification Search ............ None
See application file for complete search history.

(56) References Cited

U.S. PATENT DOCUMENTS

2004/0048267 A1* 3/2004 Rothschild et al. ............ 435/6

FOREIGN PATENT DOCUMENTS

WO    WO 02/064820 A1    8/2002

OTHER PUBLICATIONS

Smith et al. NCBI Database, GenBank Accession No. AH009246 (locus AF252504) Apr. 19, 2000.*

Smith et al. NCBI Database, GenBank Accession No. AH009246 (locus AF252504) Feb. 12, 2002.*

Smith et al. NCBI Database, GenBank Accession No. AF465178, Feb. 16, 2002.*

B.T. Page et al., Evaluation of Single-nucleotide polymorphisms in $CAPN1$ for association with meat tenderness in cattle$_{1,2}$, 2002 American Society of Animal Science. J. Anim. Sci. 2002 80:3077-3085—First made publicly available online on Dec. 20, 2002.

Brent T. Page et al., Evaluation of SNPS and haplotypes in CAPN1 for Association with meat tenderness in cattle, Plant, Animal & Microbe Genomes X Conference, Jan. 12-16, 2002, San Diego, CA.

N.G. Cullen et al., A single-nucleotide polymorphism on Calpain-1 is associated with meat tenderness in cattle, Proceedings of the New Zealand Society of Animal Production 63:53-56.

T.P.L. Smith et al., Bovine *CAPN1* maps to a region of BTA29 containing a quantitative trait locus for meat tenderness, 2000 American Society of Animal Science, J. Anim. Sci. 2000 78:2589-2594.

* cited by examiner

*Primary Examiner*—Carla J. Myers
(74) *Attorney, Agent, or Firm*—John D. Fado; Randall E. Deck; Lesley Shaw

(57) ABSTRACT

Single nucleotide polymorphisms (SNPs) in the gene encoding micromolar calcium activated neutral protease (mu-calpain) effect meat tenderness in bovine. These SNPs correspond to position 18 of exon 9 of Seq. ID No. 3, position 17 of exon 14 of Seq. ID No. 4, and position 185 on intron 19 of Seq. ID No. 4, of the CAPN1 gene encoding mu-calpain. Alleles wherein the SNP at position 18 of exon 9 encodes alanine at amino acid 316 of bovine mu-calpain, the SNP at position 17 on exon 14 encodes valine at amino acid 530 of bovine mu-calpain, and the SNP at position 185 on intron 19 is an cytosine, are all indicative of increased meat tenderness. Any one or all of these SNPs may be used as markers for selecting bovines having superior meat tenderness, and selecting animals for breeding purposes.

25 Claims, 1 Drawing Sheet

US 7,238,479 B2

SINGLE NUCLEOTIDE POLYMORPHISM MARKERS IN THE BOVINE *CAPN1* GENE TO IDENTIFY MEAT TENDERNESS

BACKGROUND OF THE INVENTION

1. Field of the Invention

The invention relates to a method for detecting genetic variations in bovine which influence meat tenderness.

2. Description of the Prior Art

Variation in meat tenderness has significant impact on consumer satisfaction with beef, however, classical selection techniques have not been effective in eliminating animals yielding undesirable palatability traits. Establishing the genetic basis for variation in meat tenderness would likely aid in the development of selection criteria for improving meat tenderness in cattle.

Currently, there is only one commercially available genetic test for meat tenderness. This test, which is marketed from Australia, tests for variation in the bovine calpastatin (CAST) gene.

The CAPN1 gene encodes a cysteine protease, micromolar calcium activated neutral protease (also known as mu-calpain), that degrades myofibrillar proteins under post mortem conditions and appears to be the primary enzyme in the post mortem tenderization process (Koohmaraie, M. 1992. The role of Ca2+-dependent proteases (calpains) in postmortem proteolysis and meat tenderness. Biochemie 74:239–245; Koohmaraie, M. 1994. Muscle proteinases and meat aging. Meat Science 36:93–104; Koohmaraie, M. 1996. Biochemical factors regulating the toughening and tenderization process of meat. Meat Sci. 43:S193–S201). Regulation of mu-calpain activity has been correlated with variation in meat tenderness (Geesink, G. H., and M. Koohmaraie. 1999. Effect of calpastatin on degradation of myofibrillar proteins by mu-calpain under postmortem conditions. J. Anim. Sci. 77:2685–2692). Bovine CAPN1 has been mapped to the telomeric end of BTA29 (Smith T. P. L. et al. 2000a. Bovine CAPN1 maps to a region of BTA29 containing a quantitative trait locus for meat tenderness. J. Anim. Sci. 78:2589–2594) and recently a quantitative locus (QTL) for tenderness was found to be segregating in this region of BTA29 in two resource populations (Casas E. et al. 2000. Quantitative trait loci affecting growth and carcass composition of cattle segregating alternate forms of myostatin. J. Anim. Sci. 78:560–569; Morris C. A. et al., 2001. Progress in DNA marker studies of beef carcass composition and meat quality in New Zealand and Australia. Proc., Assn. Advance. Anim. Breed. Genet. 14:17–22). The moderate effect (0.4 standard deviation) of this QTL on Warner-Bratzler shear force, a mechanical measurement of tenderness (AMSA, 1995. Research guidelines for cookery, sensory evaluation and instrumental tenderness measurements of fresh meat. Am. Meat Sci. Assn., Chicago, Ill.) in the U.S. Meat Animal Research Center (MARC) population supported the evaluation of CAPN1 as a candidate gene for tenderness within this population.

SUMMARY OF THE INVENTION

We have now discovered specific single nucleotide polymorphisms (SNPs) in the gene encoding micromolar calcium activated neutral protease or mu-calpain which effect meat tenderness in bovine. These SNPs correspond to position 18 of exon 9 of Seq. ID No. 3, position 17 of exon 14 of Seq. ID No. 4, and position 185 on intron 19 of Seq. ID No. 4, of the CAPN1 gene encoding mu-calpain. Alleles wherein the SNP at position 18 of exon 9 of Seq. ID No. 3 encodes alanine at amino acid 316 of bovine mu-calpain, the SNP at position 17 on exon 14 encodes valine at amino acid 530 of bovine mu-calpain, and wherein the SNP at position 185 on intron 19 is a cytosine, are all indicative of increased meat tenderness. Any one or all of these SNPs may be used as markers for selecting bovines having superior meat tenderness, and selecting animals for breeding purposes.

In accordance with this discovery, it is an object of this invention to determine SNPs in the gene encoding mu-calpain in bovine which effect meat tenderness.

It is also an object of this invention to provide methods for identifying those SNPs in the gene encoding mu-calpain in bovine which effect meat tenderness.

In accordance with this discovery, it is an object of this invention to provide methods for identifying bovine exhibiting the phenotypic trait of increased meat tenderness.

Another object of this invention is to provide methods for screening bovine to select for those animals which possess alleles of the gene encoding mu-calpain that are associated with increased meat tenderness.

Other objectives and advantages of this invention will become readily apparent from the ensuing description.

DEFINITIONS

Figure 1:
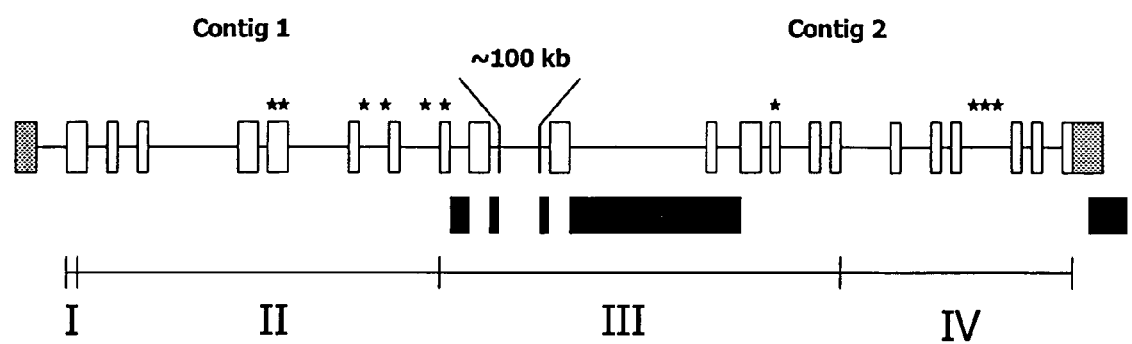
FIG. 1 shows a schematic of the CAPN1 gene as described in Example 1. The boxes represent exon sequence while the connecting lines represent the intron sequence. The approximate 100 kb intron 10 is shown as a break in the sequence. The open boxes represent coding region while the hatched boxes represent untranslated sequence. The black boxes located below the schematic of the gene indicate sequence generated from this study. Contigs 1 and 2 from this study are indicated and contig 3 is located within the ~100 kb intron. The domains of the protein are marked by Roman numerals I–IV and the set of 10 SNPs for haplotype construction are shown as stars. SNP 1 is the first star on the left followed by the rest of the SNPs in numerical order. SNPs 1 and 2 were included only in the MARC QTL population while 3–10 were included in both resource populations.

Allele: the term coined by Bateson and Saunders (1902) for characters which are alternative to one another in Mendelian inheritance (Gk. Allelon, one another; morphe, form). Now the term allele is used for two or more alternative forms of a gene resulting in different gene products and thus different phenotypes. In a haploid set of chromosomes there is only one allele at its specific locus. Diploid organisms have 2 alleles at a given locus, i.e. a normal and a mutant allele. A single allele for each gene locus is inherited separately from each parent (e.g., at a locus for eye color the allele might result in blue or brown eyes). An organism is homozygous for a gene if the alleles are identical, and heterozygous if they are different. (Birgid Schlindwein's Hypermedia Glossary of Genetic Terms).

Amplicon: a term to define the amplification product generated by the polymerase chain reaction. The physical boundaries of an amplicon extend to the base sequence at the 5' ends of each of a pair of primers (short, 18–20 oligonucleotides) in the reaction.

Centimomorgan (cM): a unit to measure the recombination frequency. One centimorgan is equal to a 1% chance that a marker at one genetic locus will be separated from a marker at a second locus due to crossing over in a single generation. In human beings, 1 centimorgan is equivalent, on average, to 1 million base pairs. (Birgid Schlindwein's Hypermedia Glossary of Genetic Terms).

Crossing over: the term coined by Morgan and Cattell (1912) for the occurrence of new combinations of linked characters. With the acceptance of the chromosome theory, the term is applied to the breaking during meiosis of one maternal and one paternal chromosome, the exchange of corresponding sections of DNA, and the rejoining of the chromosomes. This process can result in an exchange of alleles between chromosomes and gives rise to new character combinations. (Birgid Schlindwein's Hypermedia Glossary of Genetic Terms).

DNA or RNA sequence: a linear series of nucleotides connected one to the other by phosphodiester bonds between the 3' and 5' carbons of adjacent pentoses.

Genotype: the term proposed by Johannsen (1909) for the hereditary constitution of an individual, or of particular nuclei within its cells. (Birgid Schlindwein's Hypermedia Glossary of Genetic Terms).

Identity by descent: two alleles at a single locus are identical by descent if there are identical copies of the same allele in some earlier generation, i.e., both are copies that arose by DNA replication from the same ancestral sequence without any intervening mutation.

Identity by type: two alleles at a single locus are identical by type, (i.e. "the same") if they have the same phenotypic effects.

Locus: the position of a gene on a chromosome or other chromosome markers; also, the DNA at that position. The use of the term locus is sometimes restricted to main regions of DNA that are expressed. (Birgid Schlindwein's Hypermedia Glossary of Genetic Terms).

Marker: an identifiable physical location on a chromosome (e.g., restriction enzyme cutting site, gene, minisatellite, microsatellite) whose inheritance can be monitored. Markers can be expressed regions of DNA (genes) or some segment of DNA with no known coding function but whose pattern of inheritance can be determined. (Birgid Schlindwein's Hypermedia Glossary of Genetic Terms).

Nucleic acid: a deoxyribonucleotide or ribonucleotide polymer in either single- or double-stranded form, including known analogs of natural nucleotides unless otherwise indicated.

Nucleotide: a monomeric unit of DNA or RNA consisting of a sugar moiety (pentose), a phosphate, and a nitrogenous heterocyclic base. The base is linked to the sugar moiety via the glycosidic carbon (1' carbon of the pentose) and that combination of base and sugar is a nucleoside. The base characterizes the nucleotide. The four DNA bases are adenine ("A"), guanine ("G"), cytosine ("C") and thymine ("T"). The four RNA bases are A, G, C and uracil ("U").

Oligonucleotide: a single-stranded nucleic acid ranging in length from 2 to about 500 bases, usually 2–100 bases.

Phenotype: the term coined by Johannsen (1909) for the appearance (Gk. phainein, to appear) of an organism with respect to a particular character or group of characters (physical, biochemical, and physiologic), as a result of the interaction of its genotype and its environment. Often used to define the consequences of a particular mutation. (Birgid Schlindwein's Hypermedia Glossary of Genetic Terms).

Polymorphic marker or site: the locus at which divergence occurs. Preferred markers have at least two alleles, each occurring at frequency of greater than 1%, and more preferably greater than 10% or 20% of a selected population. A polymorphic locus may be as small as one base pair. Polymorphic markers include restriction fragment length polymorphisms, variable number of tandem repeats (VNTR's), hypervariable regions, minisatellites, dinucleotide repeats, trinucleotide repeats, tetranucleotide repeats, simple sequence repeats, and insertion elements such as Alu. The first identified allelic form is arbitrarily designated as the reference form and other allelic forms are designated as alternative or variant alleles. The allelic form occurring most frequently in a selected population is sometimes referred to as the wildtype form. Diploid organisms may be homozygous or heterozygous for allelic forms. A diallelic polymorphism has two forms. A triallelic polymorphism has three forms (U.S. Pat. No. 6,368,799).

Probe: a DNA fragment or an oligonucleotide capable of binding to a target nucleic acid of complementary sequence through one or more types of chemical bonds, by hybridization or complementary base pairing, usually through hydrogen bond formation. Oligonucleotides probes are often 10–50 or 15–30 bases long. An oligonucleotide probe may include natural (i.e. A, G, C, or T) or modified bases (7-deazaguanosine, inosine, etc.).

Recombination: the process by which progeny derive a combination of linked genes different from that of either parent. In higher organisms, this can occur by crossing over between their loci during meiosis. Recombination may come about through random orientation of non-homologous chromosome pairs on the meiotic spindles, from crossing-over between homologous chromosomes, from gene conversion, or by other means. (Birgid Schlindwein's Hypermedia Glossary Of Genetic Terms).

Single nucleotide polymorphism (SNP): occurrence of a polymorphic site occupied by a single nucleotide, constituting the site of variation between allelic sequences. The site is usually preceded by and followed by highly conserved sequences of the allele (e.g., sequences that vary in less than 1/100 or 1/1000 members of the populations). A single nucleotide polymorphism usually arises due to substitution of one nucleotide for another at the polymorphic site.

Specific hybridization: binding, duplexing, or hybridizing of a molecule only to a particular nucleotide sequence under stringent conditions such that the probe will hybridize to its target subsequence, but not to other sequences. Stringent conditions are sequence-dependent and are different in different circumstances. Longer sequences hybridize specifically at higher temperatures. Generally, stringent conditions are selected to be about 5° C. lower than the thermal melting point (Tm) for the specific sequence at a defined ionic strength and pH. The Tm is the temperature (under defined ionic strength, pH, and nucleic acid concentration) at which 50% of the probes complementary to the target sequence hybridize to the target sequence at equilibrium. Typically, stringent conditions include a salt concentration of at least about 0.01 to 1.0 M Na ion concentration (or other salts) at pH 7.0 to 8.3 and the temperature is at least about 30° C. for short probes (e.g., 10 to 50 nucleotides). Stringent conditions can also be achieved with the addition of destabilizing agents such as formamide. For example, conditions of 5×SSPE (750 mM NaCl, 50 mM NaPhosphate, 5 mM EDTA, pH 7.4) and a temperature of 25–30° C. are suitable for allele-specific probe hybridizations. A perfectly matched probe has a sequence perfectly complementary to a particular target sequence (U.S. Pat. No. 6,368,799).

Transition: the term proposed by Freese (1959) for a mutation caused by the substitution in DNA or RNA of one purine by the other, and similarly with the pyrimidines. (Birgid Schlindwein's Hypermedia Glossary Of Genetic Terms).

Transversion: the term proposed by Freese (1959) for a mutation caused by the substitution of a purine for a pyrimidine, and vice versa, in DNA or RNA. (Birgid Schlindwein's Hypermedia Glossary Of Genetic Terms).

GENBANK DEPOSIT

The bovine CAPN1 gene encoding micromolar calcium activated neutral protease has been completely sequenced with the exception of intron 10. The sequences of the gene flanking intron 10 have therefore been separately presented and deposited. The first 6400 bases (in the direction from 5' to 3') of the genomic DNA sequence of the CAPN1 gene encoding micromolar calcium activated neutral protease, including exons 1 through 10 and introns 1–9, has been deposited as GenBank deposit accession number AF252504. The terminal 9,800 bases (also in the direction from 5' to 3') of the CAPN1 gene, including exons 11–22 and introns 11–21, has been deposited as GenBank deposit accession number AF248054. The cDNA sequence encoding micromolar calcium activated neutral protease has been deposited as GenBank deposit accession number AF221129.

DETAILED DESCRIPTION OF THE INVENTION

As noted hereinabove, intron 10 of the bovine CAPN1 gene encoding micromolar calcium activated neutral protease (Mu-calpain) has not been completely sequenced. The sequences of the gene flanking intron 10 have therefore been separately presented. The first 6400 bases of the genomic DNA sequence of the CAPN1 gene, located on the 5' side of intron 10 and including exons 1 through 10 and introns 1–9, has been deposited in GenBank and is presented herein as Seq. ID No. 3. The terminal 9,800 bases of the CAPN1 gene, located on the 3' side of intron 10 and including exons 11–22 and introns 11–21, has also been deposited in GenBank and is presented herein as Seq. ID No. 4. The cDNA sequence encoding mu-calpain has been deposited in GenBank and is presented herein as Seq. ID No. 2. The nucleic acid sequences of exons 9 and 14, and intron 19, of the bovine CAPN1 gene are presented as Seq. ID Nos. 5, 6, and 7, respectively.

The invention is drawn to a method for determining alleles of the CAPN1 gene encoding micromolar calcium activated neutral protease (mu-calpain, the amino acid sequence of which is shown as Seq. ID No. 1) which effect meat tenderness in a bovine animal. In accordance with this method, a sample of nucleic acids from a bovine is assayed for the nucleotides at any one or combination of the SNPs in the CAPN1 gene which are disclosed herein. The SNPs of this invention correspond to position 18 of exon 9 of the CAPN1 gene (base no. 5709 of Seq. ID No. 3), position 17 of exon 14 of the CAPN1 gene (base no. 4558 of Seq. ID No. 4), and position 185 on intron 19 of the CAPN1 gene (base no. 7367 of Seq. ID No. 4). In terms of their positions on Seq. ID Nos. 5–7 representing exons 9 and 14 and intron 19, the SNPs of this invention are located at position 18 of Seq. ID No. 5, position 17 of Seq. ID No. 6, and position 185 of Seq. ID No. 7.

The SNP at position 18 on exon 9 may encode either alanine or glycine at amino acid 316 of mu-calpain, while the SNP at position 17 on exon 14 may encode valine or isoleucine at amino acid 530 of mu-calpain, and the SNP at position 185 on intron 19 may be either cytosine or thymine. Specifically, the SNP at position 18 on exon 9 may be cytosine, yielding a GCC codon for alanine, or guanine, yielding a GGC glycine codon. The SNP at position 17 on exon 14 may be guanine, yielding a GTC valine codon, or adenine, yielding am ATC isoleucine codon.

Each of the alleles wherein the polymorphism at position 18 on exon 9 of the CAPN1 gene encodes alanine at amino acid 316 of mu-calpain (i.e., the nucleotide at the SNP is cytosine), the polymorphism at position 17 on exon 14 of the CAPN1 gene encodes valine at amino acid 530 of mu-calpain (i.e., the nucleotide is guanine), and the polymorphism at position 185 on intron 19 of the CAPN1 gene wherein the nucleotide is cytosine, are independently associated with increased meat tenderness in bovine. In comparison, alleles wherein the polymorphism at position 18 on exon 9 of the CAPN1 gene encodes glycine at amino acid 316 of mu-calpain (i.e., the nucleotide is guanine), the polymorphism at position 17 on exon 14 of the CAPN1 gene encodes isoleucine at amino acid 530 of mu-calpain (i.e., the nucleotide is adenine), and the polymorphism at position 185 on intron 19 of the CAPN1 gene wherein the nucleotide is thymine, are each independently associated with relatively decreased meat tenderness in bovine.

The SNPs may be detected by assaying for the presence of the above-mentioned nucleotides in a sample of nucleic acids from a subject bovine animal at the loci of the SNPs, wherein the loci correspond to position 18 of exon 9 of the CAPN1 gene (base no. 5709 of Seq. ID No. 3), position 17 of exon 14 of the CAPN1 gene (base no. 4558 of Seq. ID No. 4), and position 185 on intron 19 of the CAPN1 gene (base no. 7367 of Seq. ID No. 4). With respect to the SNPs on exons 9 and 14, suitable nucleic acids for use in the assay include genomic DNA, cDNA, or RNA, as well as nucleic acids that encompass, or are encompassed by, Seq. ID Nos. 3 or 4 or the complement thereof. However, the skilled practitioner will recognize that suitable nucleic acids for use in the assay of the SNP on intron 19 include genomic DNA molecules that encompass, or are encompassed by, Seq. ID No. 4 or the complement thereof. It is also envisioned that the SNPs on exons 9 and 14 may also be detected by analysis of the encoded gene product, i.e., the amino acid sequence of mu-calpain in a sample obtained from the subject animal. Sample materials which may be collected from the animal for the assay include, but are not limited to, blood, tissue, cells or other biological samples from the subject.

The presence of either of the allelic forms of any of the above-described SNPs can be determined by any of a number of diagnostic assays. These assays may use otherwise known techniques, including direct sequencing of the nucleic acids in the sample, or using probes which overlap the position of the SNPs on those nucleic acids. For example, Arnold et al. (U.S. Pat. No. 6,410,231, herein incorporated by reference) is drawn to SNP detection by means of an array-based sandwich assay. Alnold et al. also makes mention of a variety of other techniques that had been previously developed for SNP detection-and analysis; specifically: Sapolsky et al. (1999) U.S. Pat. No. 5,858,659; Shuber (1997) U.S. Pat. No. 5,633,134; Dahlberg (1998) U.S. Pat. No. 5,719,028; Murigneux (1998) WO 98/30717; Shuber (1997) WO 97/10366; Murphy et al. (1998) WO 98/44157; Lander et al. (1998) WO 98/20165; Goelet et al. (1995) WO 95/12607 and Cronin et al. (1998) WO 98/30883. In addition, ligase based methods are described by Barany et al. (1997) WO 97/31256 and Chen et al. Genome Res. 1998; 8(5):549–556; mass-spectroscopy-based methods by Monforte (1998) WO 98/12355, Turano et al. (1998) WO 98/14616 and Ross et al. (1997) Anal. Chem. 15:4197–4202; PCR-based methods by Hauser, et al. (1998) Plant J. 16:117–125; exonuclease-based methods by Mundy U.S. Pat. No. 4,656,127; dideoxynucleotide-based methods by Cohen et al. WO 91/02087; Genetic Bit Analysis or GBA.TM. by Goelet et al. WO 92/15712; Oligonucleotide Ligation Assays or OLAs by Landegren et al. (1988) Science 241:1077–1080 and Nickerson et al. (1990) Proc. Natl. Acad. Sci. (USA) 87:8923–8927; and primer-guided nucleotide incorporation procedures by Prezant et al. (1992) Hum. Mutat. 1:159–164; Ugozzoli et al. (1992) GATA 9:107–112; Nyreen et al. (1993) Anal. Biochem. 208:171–175, all of which are incorporated herein by reference. Other potential assay techniques are described below. McCutchen-Maloney (U.S. Pat. No. 6,340,566, herein incorporated by reference) teaches a detection and quantization of SNPs, DNA sequence variations, DNA mutations, DNA damage and DNA mismatches using mutation binding proteins alone or as chimeric proteins with nucleases on solid supports. Also, Poponin (U.S. Pat. No. 6,376,177, herein incorporated by reference) teaches a method and apparatus for SNP detection by means of spectroscopic analysis of hybridized nucleic acid using high density nucleic acid chips. Numerous conventional assay techniques for detecting SNPs which are also suitable for use herein are described by Aguirre et al. (U.S. Pat. No. 6,428,958) and Rothenberg (U.S. Pat. No. 6,355,425) the contents of each of which are incorporated by reference herein.

The presence of the SNPs on the exons of the CAPN1 gene may be detected by assaying for the same nucleotides described above at the loci corresponding to position 18 of exon 9 of the CAPN1 gene (base no. 5709 of Seq. ID No. 3) or position 17 of exon 14 (base no. 4558 of Seq. ID No. 4), in an RNA molecule which is a transcript of a sequence encompassed by, or encompassing, the complementary strand to Seq. ID Nos. 1 or 2. Alternatively, any of the SNPs may be detected in the DNA strand complementary to Seq. ID Nos. 3 or 4 by assaying for the complementary nucleotides at the loci corresponding to position 18 of exon 9, position 17 of exon 14, or position 185 on intron 19 (base no. 7367 of Seq. ID No. 4).

As noted above, the SNPs on exons 9 and 14 of the bovine CAPN1 gene may also be detected by analysis of the mu-calpain product. For example, the alanine/glycine substitution caused by the SNP on exon 9, and the valine/isoleucine substitution caused by the SNP on exon 14, may be identified by contacting the biological samples with immunolabelling agents, such as monoclonal or polyclonal antibodies, raised against the variant protein (i.e., the protein resulting from the CAPN1 gene with the aforementioned alanine/glycine or valine/isoleucine substitutions). Such antibodies may be obtained using standard techniques and may be polyclonal or monoclonal. For instance, anti-mu-calpain antibodies are known in the art, such as those produced from clone 2H2A7C2 (1992. Exper. Cell Res. 203:5–16; 1993. J. Biol. Chem. 268:25740–25747, the contents of each of which are incorporated by reference herein) and clone 9A4H8D3 (1992, Exper. Cell Res. 203:5–16; 2000. Food Chemistry and Toxicology. 65:1318–1324; 1998. J. Anim. Sci. 76:2415–2434, the contents of each of which are incorporated by reference herein). Polyclonal antibodies can be obtained, for example, by the methods described in Ghose et al. (Methods in Enzymology. Vol. 93:326–327, 1983). A mu-calpain polypeptide, or an antigenic fragment thereof, is used as an immunogen to stimulate the production of mu-calpain reactive polyclonal antibodies in the antisera of animals such as rabbits, goats, sheep, rodents and the like. Anti-mu-calpain antibodies specific for CAPN1 gene products are raised by immunizing animals with a polypeptide spanning site of the variation (i.e., amino acids 316 or 530). Monoclonal antibodies may be obtained by the process described by Milstein and Kohler (1975. Nature. 256:495–497) or as modified by Gerhard (Monoclonal Antibodies. Plenum Press. 1980. pages 370–371). Hybridomas are screened to identify those producing antibodies that are highly specific for the selected mu-calpain enzyme immunogen, which is characteristic of increased or decreased meat tenderness.

Antibody binding may also be detected using known methods. For example, an ELISA assay utilizing a substrate (e.g., a plastic dish) coated with antigen comprising a bovine-derived biological sample containing the CAPN1 gene product. An antibody preparation specific for a known CAPN1 gene product is added to the well, whereupon the antibody will bind or fail to bind to the sample in the well. Non-binding material is washed away and a marker enzyme (e.g., horse radish peroxidase or alkaline phosphatase, coupled to a second antibody directed against the antigen-specific primary antibody) is added in excess and the non-adherent material is washed away. An enzyme substrate is added to the well and the enzyme catalyzed conversion is monitored as indicative of presence of the variant.

The SNPs in the CAPN1 gene of this invention may be used as markers for identifying bovine animals having increased meat tenderness. In a preferred embodiment, the SNPs are used as markers to select for cattle having the alleles associated with increased meat tenderness for use in breeding programs to produce progeny which will also yield meat with increased tenderness. Bovine identified as possessing any one or two of the SNPs, and most preferably all three of the SNPs associated with increased meat tenderness, would be retained for breeding. Bovine possessing SNPs associated with less tender meat would not be selected for breeding. While it is envisioned that the invention may be practiced with any species of the genus *Bos*, it is preferably practiced with *Bos taurus*.

The following examples are intended only to further illustrate the invention and are not intended to limit the scope of the invention which is defined by the claims.

EXAMPLE 1

Materials and Methods

BAC Sequencing

A random shotgun library was prepared from a Bacterial Artificial Chromosome (BAC) clone (Smith et al., 2000a, ibid; Warren W. et al. 2000. Construction and characterization of a new bovine bacterial artificial chromosome library with 10 genome-equivalent coverage. Mamm. Genome 11:662–663) containing the CAPN1 gene by partial digestion of ~5 μg BAC DNA with the restriction enzyme CviJI (0.3 units per ul) essentially as described (Gingrich J. C. et al. 1996. Partial CviJI digestion as an alternative approach to generate cosmid sublibraries for large-scale sequencing projects. Biotechniques 21:99–104). Briefly, the DNA was incubated with enzyme in a 50 μl volume for twenty minutes, the resulting DNA smear was separated on a 1% agarose gel, and fragments in the 1 to 1.5 kb range were isolated using a commercial kit (Novagen, Madison, Wis.). The eluted fragments were ligated to pBluescript vector (Stratagene, La Jolla Calif.) that had been linearized with restriction enzyme EcoRV and treated with alkaline phosphatase. Ligated fragments were transformed into Top 10 competent cells (Invitrogen, Valencia Calif.). Sequencing was performed on PCR derived templates as described (Smith T. P. L. et al. 2000b. PCR-Based setup for highthroughput cDNA library sequencing on the ABI 3700™ automated DNA sequencer. Biotechniques 29:698–700), using T7 and T3 as universal sequencing primers, on an ABI 3700 sequencer and an ABI 377 sequencer.

The sequences from BAC subclones were analyzed with the sequence assembly algorithm Phrap (Ewing B., and P. Green. 1998. Base-calling of automated sequencer traces using Phred. II. Error probabilities. Genome Res. 8:186–194; Ewing B. et al. 1998. Base-calling of automated sequencer traces using phred. I. Accuracy assessment. Genome Res. 8:175–185) to detect overlaps and form contigs. The previously published (Smith et al., 2000a, ibid) partial sequence of the bovine CAPN1 gene was included in the data set to seed formation of contigs surrounding the gene. Sequence comparisons of the contig sequences with human genomic sequence surrounding the human CAPN1 gene (GenBank accession number NT_030106.2) and the *E. coli* genome were performed using BLASTN (Altshul S. F. et al. 1990. Basic local alignment search tool. J. Mol. Biol. 215:403–410; Altschul S. F. et al. 1997. Gapped BLAST and PSI-BLAST: a new generation of protein database search programs. Nucl. Acids Res. 25:3389–3402).

Animal Sequencing and SNP Identification

Primers (Table 1) for PCR amplification were designed from the CAPN1 gene sequence (GenBank accession AF252504 and AF248054) to obtain overlapping DNA fragments of 1 to 2 kb predicted length. Production of amplicons for direct sequencing was performed in a 20 µl volume with AMPLITAQ GOLD or HOT STAR Taq polymerase enzyme following the protocols supplied by the manufacturers (Applied Biosystems Inc.; Qiagen, Inc.). Sequencing was performed using one fourth reaction volumes with BIGDYE TERMINATOR recommended by the manufacturer (Applied Biosystems Inc.), and analyzed on an ABI 3700 sequencer. Amplicons were sequenced with the amplification primers.

Sequence data were entered into the MARC database, base calls were made using Phred and the sequences aligned using Phrap (Ewing and Green, 1998, ibid; Ewing et al., 1998, ibid). SNPs were identified and tagged using the Consed viewer (Gordon D. et al., 1998. Consed: a graphical tool for sequence finishing. Genome Res. 8:195–202) as described (Heaton M. P. et al. 2001. Interleukin-8 haplotype structure from nucleotide sequence variation in commercial populations of U.S. beef cattle. Mamm. Genome 12:219–226). Genotyping was performed using a mass spectrometry-based MASSARRAY system as suggested by the manufacturer (Sequenom, Inc.), employing a PCR primer tailed with universal primer sequence in combination with a universal primer carrying a biotin tag as described (Stone R. T. et al. 2002. Use of bovine EST data and human genetic sequence to map 100 gene-specific bovine markers. Mamm. Genome 13:211–215). PCR amplification for MASSARRAY assays was carried out as outlined above except that reactions were carried out in 50 µl volumes.

Resource Populations

The MARC resource family used in this study has been previously described (Casas E. et al. 1998. Association of the muscle hypertrophy locus with carcass traits in beef cattle. J. Anim. Sci. 76:468–473). Briefly, a half-sib family was developed using a Piedmontese×Angus sire. A total of 209 offspring were produced by matings primarily to MARC III dams (¼ Angus, ¼ Hereford, ¼ Pinzgauer, and ¼ Red Poll). Dams were artificially inseminated and the offspring were born during the spring of 1995. Calves were weaned at an average of 200 days and raised from weaning to slaughter on a corn-corn silage diet. Steers were slaughtered at a commercial beef processing facility after 194 to 312 days on feed, and heifers were slaughtered after 207 to 287 days on feed. Meat tenderness was measured in all animals on the longissimus thoracis as Warner-Bratzler shear force (kg), at 3 and 14 days postmortem after belt cooking as described by Wheeler et al. (1998. Cooking and palatability traits of beef longissimus steaks cooked with belt grill on an open hearth electric broiler. J. Anim. Sci. 76:2805–2810). This family was used to detect QTL based on differences between the two paternal alleles for growth, carcass composition and meat quality traits (Casas et al., 2000, ibid; Casas E. et al. 2001. A comprehensive search for quantitative loci affecting growth and carcass composition of cattle segregating alternative forms of the myostatin gene. J. Anim. Sci. 79:854–860).

The New Zealand AgResearch resource family used in this study was the progeny of a Limousin×Australian Jersey sire. The bull's semen was imported into New Zealand for insemination of New Zealand Limousin and New Zealand Jersey cows (mainly grade animals), thus providing backcross animals of two types for a joint New Zealand-Australian DNA marker study. Importation into New Zealand of semen from this and two other bulls from the Australian "Mapping Project" (Pitchford W. S. et al. 1998. Breed and sire effects on saleable beef yield. Proc., $6^{th}$ World Congr. Genet. App. Livest. Prod. 23:117–120), provided common genetic links between New Zealand and Australian grandparents for the joint study. The cows in New Zealand were inseminated in 1995 and 1996, and calves were born in 1996 and 1997 in industry and research herds. Heifer and steer calves were collected after weaning and grown out on a research property (Tokanui Station) near AgResearch's headquarters. Further details of trial design and animal management (live calves and at slaughter) are given by Morris et al. (2001, ibid). Briefly, animals were pre-allocated to slaughter groups at 22 to 28 months of age, over 18 kill days in 1998 and 10 kill days in 1999, with pre-allocation based on breed of calf, sire, and balanced as far as possible for live weight before the first slaughter day. The right striploin (*M. Longissimus lumbarum*) was removed for tenderness measurement before stimulation of the remainder of the carcass. Each striploin was maintained at 15 C after removal. Five steak portions from the un-stimulated striploin were cut for the cooking and shear force measurements, with the first steak processed at rigor mortis, and the remainder at 1.3, 2.0, 2.3 and 4.0 days post mortem. A different technique for measuring shear force was used in the AgResearch population as shear force was measured by MIRINZ tenderometer (Fraserhurst L., and P. MacFarlane, P. 1983. A device for measuring the tenderness of meat. N.Z. Patent 190945).

Haplotype Analysis

Haplotypes inherited from the sires were established based on a selection of 10 SNPs representing genetic variation within the Piedmontese×Angus sire. Two SNPs representing predicted amino acid changes, two SNPs representing silent substitutions within the coding region, and six SNPs representing intron variation were selected out of 38 total SNPs heterozygous in the Piedmontese×Angus sire. Six of the SNPs selected reside on the half of the gene 5' to the approximately 100 kb intron 10, while the remaining four are located in the half 3' to intron 10 (FIG. 1). The haplotypes inherited by the sire from the Piedmontese grandsire and Angus grandam were identified by inferring the haplotypes based on offspring that were homozygous for all of the SNPs tested and comparing these genotype patterns with markers used in the QTL analysis. All offspring from the MARC family were genotyped for the ten SNPs, offspring from the New Zealand family were genotyped for eight of these SNPs informative in the Jersey×Limousin sire.

Dam Genotypes

Dam alleles were predicted based on the sire's haplotype and the SNP genotypes of the progeny. The effect of the allele inherited from the dam was estimated simultaneously with the effect of the paternally inherited haplotype in the MARC population using multiple regression (SAS 1998). Variation associated with the maternally inherited alleles was partitioned separately from that associated with paternal alleles in order to isolate novel variation from previously reported differences associated with paternal alleles (Casas et al., 2000, ibid). SNPs predicting valine or isoleucine ($V^{530}/I^{530}$) and glycine or alanine ($G^{316}/A^{316}$) were evaluated. The analysis provided least square means by using a model that included the effects of sex (steers or heifers), and days on feed as a covariate.

Results

BAC Sequencing

The first step in the evaluation of CAPN1 as a candidate was to obtain sufficient sequence to enable identification of SNPs within the entire coding region of the bovine gene. Partial sequence (11,055 bp) of the bovine CAPN1 gene (Smith et al., 2000a, ibid) was available, however, the reported CAPN1 sequence excluded sequences between exon 9 and exon 11. To obtain this sequence, a subclone library was made from a BAC containing the CAPN1 gene. Clones were sequenced from both ends to generate 5947 sequence reads, a predicted 10-fold coverage of the BAC. Analysis of the sequences assembled 4133 of the reads into 362 sequence contigs, with the remainder being low quality sequence reads or failing to show overlap with other sequences.

The three largest bovine contigs (containing 1776 reads), were examined by BLAST analysis. The first contig contained exons 1 to 10 of the bovine CAPN1 gene, the second contig contained exons 11 to 22 of the bovine CAPN1 gene, and the third contig shared homology to the human CAPN1 intron 10 (estimated to be approximately 100 kb based on the draft human sequence). The three contigs containing CAPN1 genomic sequence represented a total length of 43,848 bp. No matches or overlaps were found from the remaining contigs that added sequence information.

The two contigs containing coding portions of the bovine CAPN1 gene added significant new sequence, relative to the previous report by Smith et al. (2000a, ibid), within and around the exons as indicated by filled rectangles in FIG. 1. Furthermore, two significant aspects of CAPN1 gene architecture were revealed that had not been identified in the previous study. The additional sequence upstream of the 100 kb intron revealed a 130 bp intron in exon 9, that had not been detected by the exon primer-based PCR approach used previously (Smith et al., 2000a, ibid). Thus, the portion of the bovine CAPN1 gene upstream from the 100 kb intron includes 10 exons, rather than the 9 as previously reported. The second aspect involved the first intron downstream of the large intron which had been reported to be approximately 4 kb, but the new sequence data demonstrated that this intron is divided into a 2791 bp intron, 12 bp exon, and an 891 bp intron (FIG. 1). Therefore, the half of the gene downstream of the large intron includes 12 exons, rather than 10 as previously reported. In summary, the data indicate that the bovine CAPN1 gene consists of 22 exons and 21 introns. This is the same arrangement observed for the human gene by comparison of the human cDNA (accession NM_005186) and the draft genome (Lander E. S. et al. 2001. Initial sequencing and analysis of the human genome. Nat. Genet. 409:860–922) sequences (data not shown). The updated sequence information was sufficient to support primer design to scan all exons of the gene. No effort was made to completely sequence the ~100 kb intron 10. In all, more than 28 kb of sequence containing the entire coding region of the bovine CAPN1 gene was determined.

SNP Identification in MARC QTL Population

The hypothesis that CAPN1 variation underlies the QTL effect observed in the MARC resource population predicts the presence of sequence variation between the two alleles of the Piedmontese×Angus sire of the population (sire PA). To identify this variation, a set of PCR primers was designed to amplify and sequence the coding region of the gene (Table 1). A total of 12.5 kb of the gene was encompassed by 35 amplicons. All 22 exons were completely sequenced to identify coding region variation, and all but the two largest introns were included to identify sufficient numbers of SNPs to support construction of haplotypes. This procedure identified 38 SNPs in sire PA, of which five were in exons. Two of the five exon SNPs predicted amino acid variation in the mu-calpain protein, including a GCC alanine codon in exon 9 versus a GGC glycine codon (amino acid number 316), and a GTC valine codon in exon 14 versus an ATC isoleucine codon (amino acid number 530).

A set of microsatellite markers had been used previously to define the sire allele with effect on shear force measurement of meat tenderness. However, mapping the CAPN1 gene to the QTL interval (Smith et al., 2000a, ibid) did not define which allele of the gene would associate with decreased meat tenderness (increased shear force), nor did the previous analysis establish haplotypes to permit this analysis. Therefore the haplotypes of the sire were determined by genotyping of the progeny to identify homozygotes of each haplotype and permit unambiguous assignment of SNP alleles to each haplotype. This analysis demonstrated that one sire allele contained alanine at position 316 (allele $A^{316}$) and valine at position 530 (allele $V^{530}$), while the other sire allele contained glycine (allele $G^{316}$) and isoleucine (allele $I^{530}$) at those same two positions. A set of 10 SNPs heterozygous in sire PA were chosen to genotype the entire resource population, to determine the haplotype associated with increased shear force. The SNPs chosen and their alternative alleles in this bull are shown in Table 2, with the positions in the gene shown graphically in FIG. 1. We arbitrarily define allele 1 of this sire as the GTTTCGATCG (Seq. ID No. 87) haplotype containing $G^{316}$ and $I^{530}$, and allele 2 as the ACCCTCGCTA (Seq. ID No. 88) haplotype containing $A^{316}$ and $V^{530}$ with each base designation representing the allele of each SNP in the order shown in Table 2. Alleles 1 and 2 were inherited from the Piedmontese and Angus parent of the sire, respectively. Consistent with the original microsatellite-based QTL analysis, the haplotype analysis revealed that the Piedmontese allele had an effect on meat tenderness in this population (Table 3). This result suggests that the $G^{316}$ $I^{530}$ haplotype is a marker for a functional allele of CAPN1 associated with increased shear force in this population.

An alternative hypothesis for the observed effect is that CAPN1 markers are in linkage disequilibrium with a functional allele of another gene mapping to this part of BTA29. In this case, recombination will eventually break the association of the functional allele with CAPN1 haplotypes. To test whether CAPN1 alleles are the source of the meat tenderness variation, the contribution of alleles from the dams of the population were examined. If one or both of the predicted amino acid variations are markers for functional alleles with respect to shear force, then maternal inheritance should have a similar impact on phenotype. On the other hand, the association will be unlikely if the functional allele is in a different gene, since the dams are distantly related to the Piedmontese breed and an ample number of generations has occurred for recombination of the CAPN1 alleles and putative functional alleles of other genes. The dam haplotypes were inferred by subtraction of the known sire haplotype from the genotypes of the calves, and analyzed simultaneously with the sire allele as a fixed effect. Table 3 summarizes the analyses of the sire alleles and the dam alleles with regard to shear force mean differences, and their significance as measured by the p value. The magnitude of effect is measured by both shear force mean differences in the two alleles tested, and the calculated effect in standard deviations. The dam alleles containing $I^{530}$ or $V^{530}$, were analyzed separately from the dam alleles containing $G^{316}$ or $A^{316}$ as numbers of dams containing inferred genotypes for both markers were insufficient for haplotype analysis. The $G^{316}$ allele inherited from the dams was present at 86% frequency and did not show an effect on meat tenderness. The $I^{530}$ allele was present in the dams at 18% frequency and showed an effect on meat tenderness (increase in shear force day 14, p<0.04), providing strong support for the hypothesis that this SNP is in linkage disequilibrium with a functional allele.

SNP Identification in AgResearch QTL Population

A second resource population at AgResearch in New Zealand had been developed that showed evidence of a QTL on BTA29 (C. Morris, unpublished data). A reciprocal backcross population using a Jersey×Limousin sire (sire JL) revealed a significant QTL approximately centered at the map position of CAPN1, affecting MIRINZ tenderometer shear force. This resource population had a different breed composition and was raised in a different environment (New Zealand versus Nebraska), by a different production protocol, suggesting it represented a rigorous test for the association of particular CAPN1 haplotypes with meat tenderness across populations. The CAPN1 gene of the Jersey×Limousin sire was sequenced. No additional variation within the coding region was identified that would be predicted to alter the amino acid sequence of the protein. Genotypes from the 10 SNPs used in the MARC population demonstrated that sire JL was heterozygous for eight of the 10, including the two predicting amino acid variation. Genotypes for the eight informative SNPs were collected on the progeny of the resource population to define haplotypes of the bull and determine which haplotype had the effect of increased shear force. The two haplotypes are shown in Table 2, with allele 1 arbitrarily defined as the allele containing $G^{316}$ and $I^{530}$. Use of these SNP markers in a QTL analysis of the New Zealand population demonstrated that allele 1 of sire JL is associated with decreased meat tenderness (i.e., increased shear force, p<0.0001) in this Jersey×Limousin cross (Table 4). Allele 1 was derived from the Limousin grandsire and is highly similar to allele 1 of the MARC sire, providing support for the hypothesis that these SNPs represent markers of functional alleles of CAPN1.

The dam contributions for the two amino acid variants were inferred using the known sire contributions to the progeny. The shear force values as measured by the MIRINZ tenderometer test and results of the association analyses for both the dam and sire contributions to the progeny are summarized in Table 4. The analysis of the dam contributions revealed an effect for the $G^{316}$ allele similar to that observed in the sire alleles of both resource populations. No effect was observed for the $I^{530}$ allele when the dam contributions were analyzed as independent variables.

The identification of two mu-calpain variants that show effects on meat tenderness in unrelated QTL populations led to examination of the gene in a wider source of germplasm to ascertain the depth of CAPN1 diversity in cattle. The same primers previously used to amplify overlapping portions of the gene were applied to sequence a sampling of 16 beef breeds and the Holstein dairy breed represented in the MARC bovine diversity panel (described in Heaton et al., 2001, ibid). An additional 134 SNPs were detected in this panel, but none of the eleven present in exons were predicted to result in amino acid variation in the protein, nor were there any other obviously significant changes to the gene. The $I^{530}$ allele was observed in all of the breeds in the diversity panel except Brangus, and was present at an overall frequency of 30%. The $G^{316}$ allele was observed in all of the breeds represented by the diversity panel and was present at an overall frequency of 86%. The $A^{316}$ allele was not observed in Brahman, Simmental, Gelbvieh, Salers, Maine-Anjou, or Chianina breeds.

Discussion

We have characterized variation in the bovine CAPN1 gene to identify markers for alleles affecting meat tenderness. In the Piedmontese×Angus sire of the MARC resource population, a haplotype was defined by 10 SNPs that were representative of the variation observed by virtue of exonic and intronic SNPs lying in both halves of the gene separated by an intron of over 100 kb. This group of SNPs successfully determined the sire contribution to progeny, even in animals heterozygous at multiple positions and in the absence of dam genotypes. The initial study indicated that the paternally inherited haplotype containing $G^{316}$ and $I^{530}$ was associated with increased shear force in the MARC resource population. This conclusion is limited, since these were the same animals as the original quantitative study and therefore the two sire alleles of any gene in the QTL interval would be expected to show contrast in the population. However, the dam alleles of the resource population represented an ideal resource to address the possibility that the observed CAPN1 sequence variation represents useful markers for functional alleles affecting meat tenderness. The dams were from a different genetic background than the sire (Piedmontese×Angus sire vs Hereford, Angus, Pinzgauer, Red Poll composite dams), making it unlikely that an association of phenotype with CAPN1 markers in the dam alleles with phenotype would occur as a result of population stratification or breed effect. Subtraction of the sire haplotype from the progeny genotypes was an efficient means to determine the dam allele contribution, even in the absence of DNA samples from the dams.

No association with decreased meat tenderness was detected for the $G^{316}$ allele contributed from the dams in the MARC resource population, in contrast to the effect observed in the sire alleles. The low frequency of $A^{316}$ in the dams resulted in many of the progeny inheriting a $V^{530}$ and $G^{316}$ allele from the dam which is out of phase with the inheritance pattern from the sire. The inheritance of these two opposing alleles from the dam limits the conclusion that can be made when an effect is not observed. The $I^{530}$ allele, however, showed a similar effect on shear force when the dam alleles were analyzed as had been observed in the sire alleles, providing strong support for the utility of this marker. Further strong support is provided by the discovery that the $I^{530}$ allele also is correlated with increased shear force in the AgResearch population, which is comprised of 5 different breeds, raised on a separate continent, and with different management variables. The association of $I^{530}$ with decreased tenderness in three different genetic backgrounds as demonstrated by the MARC sire (Piedmontese×Angus), the MARC dams (Red Poll, Pinzgauer, Hereford, Angus) and the AgResearch sire (Jersey×Limousin) provides strong evidence for $I^{530}$ as a functional marker. The association of the $G^{316}$ allele with increased shear force in the AgResearch population was demonstrated when inherited from either the sire or the dams providing support for the utility of this marker in addition to the $I^{530}$ marker. The association of $G^{316}$ with increased shear force is demonstrated in three different genetic backgrounds as demonstrated by the MARC sire (Piedmontese×Angus), the AgResearch sire (Jersey×Limousin) from Australia, and the AgResearch dams (Jersey and Limousin) from New Zealand.

While differences were not detected in the AgResearch dams between the $I^{530}$ and $V^{530}$ alleles, the low frequency of dams contributing $I^{530}$ in the AgResearch population may have limited the ability to detect a difference in shear force values. In addition, tenderness measurements were taken only up to day 4 post mortem in this population. It is possible that differences are only detectable at day 14 post mortem as demonstrated by the MARC resource population. Similarly the low frequency of $A^{316}$ in the MARC resource population may have hindered the detection of a difference between $A^{316}$ and $G^{316}$ alleles in the MARC dams.

The overall results provide strong evidence that $I^{530}$ and $G^{316}$ are informative markers for meat tenderness variation. Both $I^{530}$ and $V^{530}$ alleles were detected in all breeds present in the diversity panel except for Brangus (note the panel has only four Brangus bull samples, and the Brahman and Angus bull samples had both alleles), with no breed appearing fixed for the $I^{530}$ allele. The observed frequency of $I^{530}$ across the entire panel was 30%, sufficiently high to suggest that selection could impact variation in meat tenderness. The observed frequency of $G^{316}$ across the entire panel was 86% with Brahman, Simmental, Gelbvieh, Salers, Maine-Anjou, and Chianina appearing fixed for the $G^{316}$ allele. However, the low number of samples from each breed does not support the precise calculation of frequency within breeds.

In addition to utility as markers, it is possible that one or both of the amino acid variations reflect a mutation that causes a functional change in the mu-calpain protease. Mu-calpain isoform containing $I^{530}$, $G^{316}$, or both may be a functionally different protein that led to variation in myofibrillar proteolysis and resulted in a difference in shear force in the two QTL populations. The $I^{530}/V^{530}$ variation represents a relatively conservative substitution of non-polar amino acids in Domain III of the protein, which currently has no known function in terms of the activity of the enzyme. However, it could potentially alter protein folding or stability, impacting autocatalysis or proteolytic activity. Moreover, a major change in the protein is unlikely to be necessary to effect the relatively small change in post mortem proteolysis underlying the variation in shear force measurement. A peptide search using NCBI BLAST of bovine Domain III revealed that human, mice, rat, rabbit, chicken, and monkey versions of mu-calpain all have isoleucine at position 530. In contrast, sequences for swine, sheep, zebrafish, and frog all have valine at this position, which is the most common allele in the beef diversity panel. The region of comparison was well conserved among species (>90%) except for chicken (66%) and zebrafish (56%). More sequencing of these other species is necessary before any conclusions could be made regarding these potential differences. Similar to the $I^{530}$ allele, the variation represented by the $G^{316}$ and $A^{316}$ alleles represent a relatively conservative substitution of non-polar amino acids. However, this variation is located in Domain II of the protein, which has been identified as the proteolysis domain. An alteration in the proteolysis domain could alter the activity of the protein, and thus effect meat tenderization. A peptide search using the region around this variation revealed that monkey, human, mice, rat, chicken and frog versions of mu-calpain do not contain glycine or alanine. The region in general is less conserved (<90%) for the species mentioned, and the presence of glycine, alanine, serine, asparagine, lysine, and glutamic acid demonstrate that this position is not highly conserved among species.

Our results demonstrate the association of the $I^{530}$ and $G^{316}$ alleles with meat tenderness in two separate populations as well as in the dam alleles of the MARC population and the AgResearch population, and are consistent with the hypothesis that variation in CAPN1 is responsible for the detection of the BTA29 QTLs in the two resource populations.

The disclosed SNPs determining amino acid variation of valine or isoleucine at position 530 and glycine or alanine at position 316 in the CAPN1 gene, are effective markers for meat tenderness variation.

EXAMPLE 2

The SNPs at position 18 of exon 9 of Seq. ID No. 3, position 17 of exon 14 of Seq. ID No. 4, and position 185 on intron 19 of Seq. ID No. 4, of the bovine CAPN1 gene were evaluated for their association with shear force in the U.S. MARC GPE Cycle VII cattle population. Shear force data was collected from meat obtained from a total of 564 steers at 3 and 14 days of carcass aging. This data is additional to that found in the two populations described in Example 1. Shear force phenotypes of *longissimus* muscle from GPE Cycle VII steers were collected by the modified Warner-Bratzler shear force method as described (Shackelford S. D. et al. 1999. Evaluation of slice shear force as an objective method of assessing beef *longissimus* tenderness; Journal of Animal Science, Vol. 77, pp 2693–2699). Sires for this population included twenty of the top sires (by number of registered offspring) in each of seven breeds, which represent the top seven breeds by numbers of registered cattle in the United States. Semen from these sires was used on a constant background of Hereford, Angus, and MARCIII dams to provide consistent genetic background for comparison. Genotypes were collected using a Sequenom® MassArray™ MALDI-TOF mass spectrometry system as recommended by the manufacturer. Primers for genotyping the three polymorphisms are given below:

Exon 9 polymorphism; G or C nucleotide (resulting in G316A amino acid substitution):

```
Forward amplification primer     (Seq. ID No. 78)
5' CGTTGGATGGAGCTGGCCCTCATAAGATAA 3'

Reverse amplification primer     (Seq. ID No. 79)
5' GACGTTGGATGCCCATCCTCCATCTTGACC 3'

Probe primer                     (Seq. ID No. 80)
5' CCTCGGAGTGGAACG 3'
```

The C nucleotide allele (resulting in Alanine amino acid) is associated with reduced shear force (see results below).

Exon 14 polymorphism; A or G nucleotide (resulting in V530I amino acid substitution):

```
Forward amplification primer     (Seq. ID No. 81)
5' GACGTTGGATGCGAGCCCAACAAGGAAGGT 3'

Reverse amplification primer     (Seq. ID No. 82)
5' CGTTGGATGGTGACTTTGTGCTGCGTTTCT 3'

Probe primer                     (Seq. ID No. 83)
5' GGGGAGATTGGCCTGGA 3'
```

The G nucleotide allele (resulting in Valine amino acid) is associated with reduced shear force (see results below).

Intron 19 polymorphism; T or C nucleotide (does not alter amino acid sequence of protein):

```
Forward amplification primer
5' GCAGCATGAGTGCCTATGAA 3'        (Seq. ID No. 84)
Reverse amplification primer
5' CAGGCAGCACACGAAGTTG 3'         (Seq. ID No. 85)
Probe primer
5' TGCCTTTTTCTCCTGGTAAC 3'        (Seq. ID No. 86)
```

The C nucleotide allele is associated with reduced shear force (see results below).

Genotype frequencies in the GPE Cycle VII steers for each SNP:

| | | |
|---|---|---|
| Exon 9 (G or C): | CC = 4% | (Alanine) |
| | CG = 36% | |
| | GG = 60% | (Glycine) |
| Exon 14 (A or G): | AA = 9% | (Isoleucine) |
| | AG = 38% | |
| | GG = 53% | (Valine) |
| Intron 19 (T or C): | TT = 14% | |
| | CT = 37% | |
| | CC = 49% | |

Mean shear force for each genotype by SNP in the GPE Cycle VII population:

| | |
|---|---|
| Exon 9 (G or C): | CC = 3.92 ± 0.19 kg |
| | GC = 4.08 ± 0.07 kg |
| | GG = 4.35 ± 0.05 kg |
| | P value < 0.0016 |
| | Approximate maximum effect on shear force 0.42 kg (0.92 lbs) |
| Exon 14 (A or G): | AA = 4.46 ± 0.11 kg |
| | AG = 4.35 ± 0.07 kg |
| | GG = 4.17 ± 0.06 kg |
| | P value < 0.0094 |
| | Approximate maximum effect on shear force 0.21 kg (0.46 lbs) |
| Intron 19 (T or C): | TT = 4.63 ± 0.14 kg |
| | TC = 4.40 ± 0.09 kg |
| | CC = 4.19 ± 0.08 kg |
| | P value < 0.0024 |
| | Approximate maximum effect on shear force 0.44 kg (0.97 lbs) |

It is understood that the foregoing detailed description is given merely by way of illustration and that modifications and variations may be made therein without departing from the spirit and scope of the invention.

TABLE 1

Primer pairs used for amplification of genomic CAPN1

| Forward Primer | Reverse Primer | Location in CAPN1* | SEQ. ID NO. |
|---|---|---|---|
| CTGCTGCCCCTGGTTAAA | GGCCAAGCTGGGGAACG | E1 | 8, 9 |
| GCCGAGGAGATACCGTGAA | CTGGCCCAGGTACTTGATGG | I1 | 10, 11 |
| GATCCTTCAACCCGTCTC | AGGTACTTGATGGCATTTTC | I1 partial, E2 partial | 12, 13 |
| CTGATCCTTCAACCCGTCTC | GGTGCCCCTCAACTTACAGA | I1 partial, E2, I2, E3, I3 partial | 14, 15 |
| GGTAGCATTGGGTGAGGGTA | AGTGCCATACTGGGGAGAAC | E2, I2, E3, I3 partial | 16, 17 |
| GTTCTCAAACCCCCAGTTC | ATGTCTCTTTCCCAAAACGA | I3, E4, I4 partial | 18, 19 |
| TGGCTACGCTGGCATCTTC | TTGCAAAGCCCTTGGACC | I4 partial | 20, 21 |
| ATGGCTACGCTGGCATCTTC | GTGGGTCCCGTCAAGTGAA | I4 partial | 22, 23 |
| ACTTGACGGGACCCACAGTG | GGAGGAGGGCACAGTGAAT | I4 partial | 24, 25 |
| CGCATTTTCATTCCACATCT | ACCGCTAGGAGACTCAGGTC | I4 partial, E5, I5, E6 | 26, 27 |
| GCTGTGGCAGTTTGGTGAGTG | CAGGGCCTTGAGGATGATGTT | E5 partial, I5 E6 partial | 28, 29 |
| GCTGTGGCAGTTTGGTGAG | GAGAAGAGGGGTGAGCAGAG | E5 partial, I5, E6, I6 partial | 30, 31 |
| TCTGAGGGCTTTGAGGACTT | ATCTGGCCCTGGTAGTTCAC | I6, E7, I7 | 32, 33 |
| CCCCGTGACCTTCAGCAGCAC | GTTGCGGAACCTCTGGCTCTTGAG | I7 partial, E8, I8, E9, I9 | 34, 35 |
| GGACTCTCGCCCAAAGAT | CCAGGTGCCCTCATACAG | I7 partial, E8, I8, E9, I9 | 36, 37 |

TABLE 1-continued

Primer pairs used for amplification of genomic CAPN1

| Forward Primer | Reverse Primer | Location in CAPN1* | SEQ. ID NO. |
|---|---|---|---|
| GCTGTGCCATGTCTCTTGA | CTGGACAGCAAGGAAGTCTC | E10 | 38, 39 |
| CCCCTGGCTGCCTTAGTTCT | AGATCCCCTTTGCTCACTGG | E11 | 40, 41 |
| CCATAGGCTTCGCTGTCTAC | GGCCACGTGTGTTCAAG | I11, E12 | 42, 43 |
| TGGGCCCCTGTGTGG | ATGGGCAAACAATGGAAACA | E12, I12 partial | 44, 45 |
| GCAGGCAGGGCTTTTACA | CTCTGAGAAGAAACGCAGCA | E13 | 46, 47 |
| GAGCCCAACAAGGAAGGT | AATACAGCCCAATGATGAGG | I13, E14, I14 partial | 48, 49 |
| GGTCCGAGCAGTTCATCAAC | ACTTGCTGGAGAGGGAAGGT | I13, E14, I14 partial | 50, 51 |
| GTCCAGGCCAATCTCCCC | AGCTCCTTGACGCTGATCTC | I14, E15, I16 | 52, 53 |
| TCATCATTGGGCTGTATTTCC | GCTGCGTCGGGTCTTG | I14 partial, E15, I15, E16, I16 partial | 54, 55 |
| GACATGGAGATCAGCGTCAA | GCAGGGAAGGGGGTCAC | I16 partial | 56, 57 |
| CCTCTTAAATTCCTCTTGCCAGAC | GAAAACTCCACAGCGTAAACCAG | I16 partial, E17, E17 partial | 58, 59 |
| CCAGCACCGGTCCTTTTTAC | GAGGTAGGGGAGGGAGAA | I16 partial, E17, E17 partial | 60, 61 |
| TTCAGCCTGGAGTCCTGC | CATGCTGCCCGACTTGTC | I17, E18, I18 | 62, 63 |
| CTGGTTTACGCTGTGGAGTT | CCTGGCCTCATCCTGAA | E18, I18, E19, I19 partial | 64, 65 |
| GCAGCATGAGTGCCTATGAA | CAGGCAGCACACGAAGTTG | I19 | 66, 67 |
| TCACCCTCACAGTCCCACTT | GGGCCACTCTTACCTCCTCT | I19 partial, E20, I20, E21 | 68, 69 |
| GACCTGGCCGTGGACTT | GCAGAGGAGCATAGCAAGG | I20, E21, I21 | 70, 71 |
| GGGCAGTGGGTTTTTCTCAC | GCCTCTGGTATCCCCGTAAC | I21 partial, E22 partial | 72, 73 |
| CCTCTGCCCTCCTCGTC | CTGGTATCCCCGTAACTCAGT | E22 partial | 74, 75 |
| TGACCATGTTTGCGTGAGAC | ATGTGGGACCTCAGCAGTGT | E22 | 76, 77 |

*E = Exon, I = Intron

TABLE 2

Ten SNPs used to generate the haplotypes for the two resource population sires, in the order of location starting from the 5' end of the CAPN1 gene.

| SNP # | SEQUENCE*** | LOCATION | MARC Allele 1 (Piedmontese) | MARC Allele 2 (Angus) | AgResearch Allele 1 (Limousin) | AgResearch Allele 2 (Jersey) | SEQ. ID NO. |
|---|---|---|---|---|---|---|---|
| 1 | CAGCACRTCTGAG | EXON 6 | G | A | A | A | 89 |
| 2 | CACCGGYGGAGTC | EXON 6 | T | C | C | C | 90 |
| 3 | AGCTGCYTCTCTC | INTRON 7 | T | C | T | C | 91 |
| 4 | GCTGGGYTCTGTG | INTRON 7 | T | C | T | C | 92 |
| 5 | TGTGACYGGGTCT | INTRON 8 | C | T | C | T | 93 |
| 6* | GGAACGSCTGGA | EXON 9 | G (Ala) | C (Gly) | G (Ala) | C (Gly) | 94 |
| 7 | GACCAGR**TCCAGG | EXON 14 | A (Ile) | G (Val) | A (Ile) | G (Val) | 95 |
| 8 | GGTAACYGTTAGC | INTRON 19 | T | C | T | C | 96 |

TABLE 2-continued

Ten SNPs used to generate the haplotypes for the
two resource population sires, in the order of location
starting from the 5' end of the CAPN1 gene.

| SNP # | SEQUENCE*** | LOCATION | MARC Allele 1 (Piedmontese) | MARC Allele 2 (Angus) | AgResearch Allele 1 (Limousin) | AgResearch Allele 2 (Jersey) | SEQ. ID NO. |
|---|---|---|---|---|---|---|---|
| 9 | AGTACTYTTGCCT | INTRON 19 | C | T | C | T | 97 |
| 10 | TTCCGARCAGATG | INTRON 19 | G | A | G | A | 98 |

*predicted glycine to alanine amino acid substitution
**predicted valine to isoleucine amino acid substitution
***R = A or G, Y = C or T, and S = C or G

TABLE 3

Least square mean, standard error and probability values
for meat tenderness measured as Warner-Bratzler
shear force (kg) at 3 and 14 days post mortem.

| Alleles | Number of progeny* | Shear Force Day 3 | Shear Force Day 14 |
|---|---|---|---|
| Sire | | | |
| 1 (Piedmontese) | 83 | 4.73 ± 0.1 kg | 3.52 ± 0.07 kg |
| 2 (Angus) | 94 | 4.38 ± 0.09 kg | 3.26 ± 0.06 kg |
| Mean shear force difference | | 0.35 kg | 0.26 kg |
| Effect | | 0.4 SD** | 0.43 SD |
| P value | | 0.0071 | 0.0046 |
| Dam | | | |
| $I^{530}$ | 30 | 4.62 ± 0.16 kg | 3.61 ± 0.1 kg |
| $V^{530}$ | 137 | 4.55 ± 0.08 kg | 3.35 ± 0.05 kg |
| Mean shear force difference | | 0.08 kg | 0.25 kg |
| Effect | | 0.09 SD | 0.42 SD |
| P value | | 0.68 | 0.034 |
| Dam | | | |
| $G^{316}$ | 141 | 4.6 ± 0.08 kg | 3.34 ± 0.05 kg |
| $A^{316}$ | 23 | 4.47 ± 0.2 kg | 3.6 ± 0.13 kg |
| Mean shear force difference | | 0.13 kg | 0.26 kg*** |
| Effect | | 0.14 SD | 0.42 SD |
| P value | | 0.555 | 0.08 |

*Number of progeny inheriting indicated allele.
**SD = Standard Deviation.
***Note that the difference is in the opposite direction from all other shear force mean differences listed.

TABLE 4

Least square mean, standard error, and probability values for
meat tenderness measured as MIRINZ Tenderometer
shear force (kg) at 1.3, 2.0 and 2.3 days post mortem.

| Alleles | Number of progeny* | Shear force (kg) at days post-slaughter | | |
|---|---|---|---|---|
| | | Day 1.3 | Day 2.0 | Day 2.3 |
| Sire | | | | |
| 1 (Limousin) | 31 | 12.01 ± 0.36 kg | 8.55 ± 0.24 kg | 7.68 ± 0.19 kg |
| 2 (Jersey) | 50 | 9.75 ± 0.27 kg | 6.86 ± 0.18 kg | 6.33 ± 0.15 kg |
| Diff | | 2.26 ± 0.45 kg | 1.69 ± 0.30 kg | 1.35 ± 0.24 kg |
| Effect | | 1.13 SD** | 1.3 SD | 1.27 SD |
| P value | | 3.00E−06 | 2.00E−07 | 3.00E−07 |
| Dam | | | | |
| $I^{530}$ | 16 | 11.36 ± 0.53 kg | 8.08 ± 0.35 kg | 7.20 ± 0.29 kg |
| $V^{530}$ | 58 | 10.77 ± 0.29 kg | 7.72 ± 0.19 kg | 6.99 ± 0.16 kg |
| Diff | | 0.58 ± 0.65 kg | 0.37 ± 0.43 kg | 0.20 ± 0.35 kg |
| Effect | | 0.27 SD | 0.26 SD | 0.17 SD |
| P value | | 0.37 | 0.40 | 0.57 |
| Dam | | | | |
| $G^{316}$ | 39 | 11.51 ± 0.30 kg | 8.02 ± 0.20 kg | 7.37 ± 0.16 kg |
| $A^{316}$ | 34 | 10.12 ± 0.35 kg | 7.29 ± 0.23 kg | 6.58 ± 0.19 kg |
| Diff | | 1.38 ± 0.48 kg | 0.73 ± 0.32 kg | 0.79 ± 0.26 kg |
| Effect | | 0.70 SD | 0.56 SD | 0.75 SD |
| P value | | 0.0049 | 0.026 | 0.003 |

*Number of progeny inheriting indicated allele.
**SD = Standard Deviation.

We claim:

1. A method for determining one or more alleles of the gene encoding micromolar calcium activated neutral protease effecting meat tenderness in a bovine animal, comprising:
   (1) assaying a sample of nucleic acids from a bovine for the presence of one or more single nucleotide polymorphisms in the bovine CAPN1 gene encoding micromolar calcium activated neutral protease, wherein said single nucleotide polymorphisms are selected from the group consisting of (a) a quanine or cytosine at position 18 of exon 9 of Seq. ID No. 3, (b) an adenine or quanine at position 17 of exon 14 of Seq. ID No. 4, and (c) a thymine or cytosine at position 185 on intron 19 of Seq. ID No. 4, and
   (2) selecting and removing from breeding bovine having a polymorphism selected from the group consisting of (i) a polymorphism at position 18 on exon 9 encoding glycine at amino acid 316 of said bovine micromolar calcium activated neutral protease, (ii) a polymorphism at position 17 on exon 14 encoding isoleucine at amino acid 530 of said bovine micromolar calcium activated neutral protease, and (iii) a polymorphism consisting of thymine at position 185 on intron 19.

2. The method of claim 1, wherein said bovine comprises cattle.

3. The method of claim 1, wherein said nucleic acid is a DNA molecule that comprises Seq. ID No. 3 or the complement thereof.

4. The method of claim 3 comprising assaying said DNA molecule for said single nucleotide polymorphism at position 18 on exon 9, and wherein the nucleotide at said position 18 on exon 9 is cytosine.

5. The method of claim 3 comprising assaying said DNA molecule for said single nucleotide polymorphism at position 18 on exon 9, and wherein the nucleotide at said position 18 on exon 9 is guanine.

6. The method of claim 1, wherein said nucleic acid is a RNA molecule that is a transcript of a sequence that comprises Seq. ID No. 3 or the complement thereof.

7. The method of claim 6 comprising assaying said RNA molecule for said single nucleotide polymorphism at position 18 on exon 9, and wherein the nucleotide at said position 18 on exon 9 is cytosine.

8. The method of claim 6 comprising assaying said RNA molecule for said single nucleotide polymorphism at position 18 on exon 9, and wherein the nucleotide at said position 18 on exon 9 is guanine.

9. The method of claim 1, wherein said nucleic acid is a DNA molecule that comprises Seq. ID No. 4 or the complement thereof.

10. The method of claim 9 comprising assaying said DNA molecule for said single nucleotide polymorphism at position 17 on exon 14, and wherein the nucleotide at said position 17 on exon 14 is guanine.

11. The method of claim 9 comprising assaying said DNA molecule for said single nucleotide polymorphism at position 17 on exon 14, and wherein the nucleotide at said position 17 on exon 14 is adenine.

12. The method of claim 1, wherein said nucleic acid is a RNA molecule that is a transcript of a sequence that comprises Seq. ID No. 4 or the complement thereof.

13. The method of claim 12 comprising assaying said RNA molecule for said single nucleotide polymorphism at position 17 on exon 14, and wherein the nucleotide at said position 17 on exon 14 is guanine.

14. The method of claim 12 comprising assaying said RNA molecule for said single nucleotide polymorphism at position 17 on exon 14, and wherein the nucleotide at said position 17 on exon 14 is adenine.

15. The method of claim 1, wherein said nucleic acid is a genomic DNA molecule that comprises Seq. ID No. 4 or the complement thereof.

16. The method of claim 15 comprising assaying said genomic DNA molecule for said single nucleotide polymorphism at position 185 on intron 19, and wherein the nucleotide at said position 185 on intron 19 is cytosine.

17. The method of claim 15 comprising assaying said genomic DNA molecule for said single nucleotide polymorphism at position 185 on intron 19, and wherein the nucleotide at said position 185 on intron 19 is thymine.

18. A method for identifying the genotypic status of one or more single nucleotide polymorphisms in bovine effecting meat tenderness comprising:
   a) obtaining a nucleic acid sample from a bovine;
   b) assaying said nucleic acid sample for the presence of one or more single nucleotide polymorphisms in the bovine CAPNI gene encoding micromolar calcium activated neutral protease, wherein said single nucleotide polymorphisms are selected from the group consisting of (1) a guanine or cytosine at position 18 of exon 9 of Seq. ID No. 3, (2) an adenine or guanine at position 17 of exon 14 of Seq. ID No. 4, and (3) a thymine or cytosine at position 185 on intron 19 of Seq. ID No. 4, and said polymorphism at position 18 on exon 9 encodes either alanine or glycine at amino acid 316 of said bovine micromolar calcium activated neutral protease, and said polymorphism at position 17 on exon 14 encodes valine or isoleucine at amino acid 530 of said bovine micromolar calcium activated neutral protease; and
   c) selecting and removing from breeding bovine having a polymorphism selected from the group consisting of (i) a polymorphism at position 18 on exon 9 encoding glycine at amino acid 316 of said bovine micromolar calcium activated neutral protease, (ii) a polymorphism at position 17 on exon 14 encoding isoleucine at amino acid 530 of said bovine micromolar calcium activated neutral protease, and (iii) a polymorphism consisting of thymine at position 185 on intron 19.

19. The method of claim 18 further comprising selecting bovine for breeding that have a polymorphism at position 18 on exon 9 encoding alanine at amino acid 316 of said bovine micromolar calcium activated neutral protease.

20. The method of claim 18 further comprising selecting bovine for breeding that have a polymorphism at position 17 on exon 14 encoding valine at amino acid 530 of said bovine micromolar calcium activated neutral protease.

21. The method of claim 18 further comprising selecting bovine for breeding that have a polymorphism consisting of cytosine at position 185 on intron 19.

22. The method of claim 18 further comprising selecting bovine for breeding that have a polymorphism selected from the group consisting of (i) a polymorphism at position 18 on exon 9 encoding alanine at amino acid 316 of said bovine micromolar calcium activated neutral protease, (ii) a polymorphism at position 17 on exon 14 encoding valine at amino acid 530 of said bovine micromolar calcium activated neutral protease, and (iii) a polymorphism consisting of cytosine at position 185 on intron 19.

23. A method for identifying one or more mutations in micromolar calcium activated neutral protease of bovine, which said mutations effect meat tenderness, comprising:
  (a) determining the presence of either alanine or glycine at amino acid 316 of said bovine micromolar calcium activated neutral protease, or determining the presence of valine or isoleucine at amino acid 530 of said bovine micromolar calcium activated neutral protease (Seq. ID No. 1), or both, and
  (b) selecting and removing from breeding bovine having glycine at amino acid 316 of said bovine micromolar calcium activated neutral protease, or isoleucine at amino acid 530 of said bovine micromolar calcium activated neutral protease.

24. The method of claim 23 wherein the presence of alanine at amino acid 316 of said bovine micromolar calcium activated neutral protease is indicative of increased meat tenderness.

25. The method of claim 23 wherein the presence of valine at amino acid 530 of said bovine micromolar calcium activated neutral protease is indicative of increased meat tenderness.

* * * * *

SEQUENCE LISTING

<160> NUMBER OF SEQ ID NOS: 98

<210> SEQ ID NO 1
<211> LENGTH: 716
<212> TYPE: PRT
<213> ORGANISM: Bos taurus

<400> SEQUENCE: 1

```
Met Ala Glu Glu Phe Ile Thr Pro Val Tyr Cys Thr Gly Val Ser Ala
 1               5                  10                  15

Gln Val Gln Lys Gln Arg Ala Lys Glu Leu Gly Leu Gly Arg His Glu
            20                  25                  30

Asn Ala Ile Lys Tyr Leu Gly Gln Asp Tyr Glu Gln Leu Arg Val His
        35                  40                  45

Cys Leu Gln Arg Gly Ala Leu Phe Arg Asp Glu Ala Phe Pro Pro Val
    50                  55                  60

Pro Gln Ser Leu Gly Phe Lys Glu Leu Gly Pro Asn Ser Ser Lys Thr
65                  70                  75                  80

Tyr Gly Ile Lys Trp Lys Arg Pro Thr Glu Leu Phe Ser Asn Pro Gln
                85                  90                  95

Phe Ile Val Asp Gly Ala Thr Arg Thr Asp Ile Cys Gln Gly Ala Leu
            100                 105                 110

Gly Asp Cys Trp Leu Leu Ala Ala Ile Ala Ser Leu Thr Leu Asn Asp
        115                 120                 125

Thr Leu Leu His Arg Val Val Pro His Gly Gln Ser Phe Gln Asp Gly
    130                 135                 140

Tyr Ala Gly Ile Phe His Phe Gln Leu Trp Gln Phe Gly Glu Trp Val
145                 150                 155                 160

Asp Val Val Val Asp Asp Leu Leu Pro Thr Lys Asp Gly Lys Leu Val
                165                 170                 175

Phe Val His Ser Ala Gln Gly Asn Glu Phe Trp Ser Ala Leu Leu Glu
            180                 185                 190

Lys Ala Tyr Ala Lys Val Asn Gly Ser Tyr Glu Ala Leu Ser Gly Gly
        195                 200                 205

Ser Thr Ser Glu Gly Phe Glu Asp Phe Thr Gly Gly Val Thr Glu Trp
    210                 215                 220

Tyr Glu Leu Arg Lys Ala Pro Ser Asp Leu Tyr Asn Ile Ile Leu Lys
225                 230                 235                 240

Ala Leu Glu Arg Gly Ser Leu Leu Gly Cys Ser Ile Asp Ile Ser Ser
                245                 250                 255

Ile Leu Asp Met Glu Ala Val Thr Phe Lys Lys Leu Val Lys Gly His
            260                 265                 270

Ala Tyr Ser Val Thr Gly Ala Lys Gln Val Asn Tyr Gln Gly Gln Met
        275                 280                 285

Val Asn Leu Ile Arg Met Arg Asn Pro Trp Gly Glu Val Glu Trp Thr
    290                 295                 300

Gly Ala Trp Ser Asp Gly Ser Ser Glu Trp Asn Gly Val Asp Pro Tyr
305                 310                 315                 320

Met Arg Glu Gln Leu Arg Val Lys Met Glu Asp Gly Glu Phe Trp Met
                325                 330                 335

Ser Phe Arg Asp Phe Met Arg Glu Phe Thr Arg Leu Glu Ile Cys Asn
            340                 345                 350

Leu Thr Pro Asp Ala Leu Lys Ser Gln Arg Phe Arg Asn Trp Asn Thr
```

-continued

```
                355                 360                 365
Thr Leu Tyr Glu Gly Thr Trp Arg Arg Gly Ser Thr Ala Gly Gly Cys
    370                 375                 380

Arg Asn Tyr Pro Ala Thr Phe Trp Val Asn Pro Gln Phe Lys Ile Arg
385                 390                 395                 400

Leu Glu Glu Thr Asp Pro Asp Pro Asp Tyr Gly Gly Arg Glu
                405                 410                 415

Ser Gly Cys Ser Phe Leu Leu Ala Leu Met Gln Lys His Arg Arg Arg
            420                 425                 430

Glu Arg Arg Phe Gly Arg Asp Met Glu Thr Ile Gly Phe Ala Val Tyr
        435                 440                 445

Glu Val Pro Pro Glu Leu Met Gly Gln Pro Ala Val His Leu Lys Arg
    450                 455                 460

Asp Phe Phe Leu Ser Asn Ala Ser Arg Ala Arg Ser Glu Gln Phe Ile
465                 470                 475                 480

Asn Leu Arg Glu Val Ser Thr Arg Phe Arg Leu Pro Pro Gly Glu Tyr
                485                 490                 495

Val Val Val Pro Ser Thr Phe Glu Pro Asn Lys Glu Gly Asp Phe Val
            500                 505                 510

Leu Arg Phe Phe Ser Glu Lys Ser Ala Gly Thr Gln Glu Leu Asp Asp
        515                 520                 525

Gln Val Gln Ala Asn Leu Pro Asp Glu Gln Val Leu Ser Glu Glu Glu
    530                 535                 540

Ile Asp Glu Asn Phe Lys Ser Leu Phe Arg Gln Leu Ala Gly Glu Asp
545                 550                 555                 560

Met Glu Ile Ser Val Lys Glu Leu Arg Thr Ile Leu Asn Arg Ile Ile
                565                 570                 575

Ser Lys His Lys Asp Leu Arg Thr Thr Gly Phe Ser Leu Glu Ser Cys
            580                 585                 590

Arg Ser Met Val Asn Leu Met Asp Arg Asp Gly Asn Gly Lys Leu Gly
        595                 600                 605

Leu Val Glu Phe Asn Ile Leu Trp Asn Arg Ile Arg Asn Tyr Leu Ser
    610                 615                 620

Ile Phe Arg Lys Phe Asp Leu Asp Lys Ser Gly Ser Met Ser Ala Tyr
625                 630                 635                 640

Glu Met Arg Met Ala Ile Glu Phe Ala Gly Phe Lys Leu Asn Lys Lys
                645                 650                 655

Leu Tyr Glu Leu Ile Ile Thr Arg Tyr Ser Glu Pro Asp Leu Ala Val
            660                 665                 670

Asp Phe Asp Asn Phe Val Cys Cys Leu Val Arg Leu Glu Thr Met Phe
        675                 680                 685

Arg Phe Phe Lys Thr Leu Asp Thr Asp Leu Asp Gly Val Val Thr Phe
    690                 695                 700

Asp Leu Phe Lys Trp Leu Gln Leu Thr Met Phe Ala
705                 710                 715

<210> SEQ ID NO 2
<211> LENGTH: 2948
<212> TYPE: DNA
<213> ORGANISM: Bos taurus
<220> FEATURE:
<221> NAME/KEY: variation
<222> LOCATION: (1665)

<400> SEQUENCE: 2
```

-continued

```
gctctcgcgg agttggccca gcgtctgcgg aggagggccg aggagatacc gtgaattaga      60
gagatcgtcg gagaaggatg gccgaggagt tcatcactcc ggtgtactgc accggggtgt     120
ctgcacaagt gcagaagcag cgggccaagg agctgggcct gggccgccat gaaaatgcca     180
tcaagtacct gggccaggat tacgagcagc tgcgggttca ctgcctgcaa agaggggccc     240
ttttccgtga cgaggctttc cccccagtgc cccagagcct gggcttcaag gagctgggcc     300
ccaactcctc caaaacctat ggcatcaagt ggaagcgtcc cacggagctg ttctcaaacc     360
cccagttcat cgtggatgga gccacccgca cggacatctg ccaggcgcag ctgggggact     420
gttggctcct ggctgccatc gcctccctta ccctcaatga caccctcctg caccgagtag     480
ttccacatgg ccaaagcttc caggatggct acgctggcat cttccatttc cagctgtggc     540
agtttggtga gtgggtggat gtggtggtgg atgacctgct gcccaccaag gacgggaagc     600
tggtgtttgt gcactctgcc caaggcaacg agttctggag cgccctgctg agaaagcct      660 atgccaaggt gaacggcagc tacgaggccc tctcaggagg cagcacatct gagggctttg     720
aggacttcac cggcggagtc accgagtggt acgagctgcg caaggcgccc agcgacctct     780
acaacatcat cctcaaggcc ctggagcgtg ctccctgct gggctgctcc atcgatatct      840
ccagcattct ggacatggag gctgtcacct tcaagaagct ggtgaagggc cacgcctact     900
ctgtgaccgg ggccaaacag gtgaactacc agggccagat ggtgaacctg atccggatgc     960
ggaacccctg gggcgaggtg gagtggacag agcctggagt gacggctcc tcggagtgga    1020 acgscgtgga cccttacatg cgggagcagc tccgggtcaa gatggaggat ggggagttct    1080
ggatgtcatt ccgagacttc atgcgtgaat tcacccgcct ggagatctgc aacctgacac    1140
ccgacgcgct caagagccag aggttccgca actggaacac caccctgtat gagggcacct    1200
ggcggcgggg gagcaccgcg gggggctgcc gcaactaccc agccactttc tgggtgaacc    1260
cccagttcaa gatccggctg gaggagacg atgacccgga ccccgacgac tacgggggtc    1320
gcgagtcagg ctgcagcttc ctgctcgccc tcatgcagaa gcaccgccgt cgggagcgcc    1380
gtttcggccg tgacatggag accataggct tcgctgtcta cgaggtccct ccggagctga    1440
tgggccagcc ggccgtgcat ctgaagcggg acttcttcct gtccaacgcc tcccgggccc    1500
ggtccgagca gttcatcaac ctgcgggagg tcagcacccg cttccgcctg ccgcctgggg    1560
agtacgtggt ggtgccctcc accttcgagc ccaacaagga aggtgacttt gtgctgcgtt    1620
tcttctcaga gaagagcgca gggacccaag agctggatga ccagrtccag gccaatctcc    1680
ccgacgagca agtgctctca gaagaggaga ttgatgagaa cttcaagtcc ctcttcagac    1740
aactggcagg ggaggacatg gagatcagcg tcaaggagct gcggaccatc ctcaacagga    1800
tcatcagcaa acacaaagac ctgcggacca cgggcttcag cctggagtcc tgccgcagca    1860
tggtcaacct catggatcgc gacggcaatg gcaaactggg cctggtggag ttcaacatcc    1920 tatgaaccg gatccggaat tacctgtcca tcttccggaa gtttgacctg acaagtcgg     1980 gcagcatgag tgcctatgaa atgcggatgg ccattgagtt tgcaggcttc aagctcaaca    2040
agaagctgta cgagctcatt atcacccgct actcggagcc cgacctggcc gtggacttcg    2100
acaacttcgt gtgctgcctg gtgcggctgg agaccatgtt ccgttttttc aaaactctgg    2160
acactgatct ggatggagtg gtgacctttg acttgtttaa gtggttacag ctgaccatgt    2220
ttgcgtgaga cgggggctca ggcccccttg ctatgctcct ctgccctcct cgtccaccaa    2280
gccatgcctt cctgcgacgc cacaccaggc cacaccagct gcaagtgcct tccttggagc    2340
aggaggcggc ctcgacctcc tgtcccctcg cctctcagcc gccgtgtttc atttgctctg    2400
```

-continued

```
ggcagagccg tggggccctc cctgcctcca cccggcccct ccggtcgcca gaccagggag   2460
gcagctttcg ctagttcctg cctcaggatg gggctccccg gggagctggg ggccccaagc   2520
ctcccacatc ctgacgtgtc ctctctcctg ccccacagg ccaccctcc ccccctcccc    2580 cacctacaca ctttataacc actagctgtg caacagtctg cagtctagac ctgtggagcc   2640
ccctcccagc tggggccccc tccccaggac tgggaacgcc tgttcgtgcc tgtgcggaag   2700
ccaatgctcc cctctgcccc atgaccccc tagcctgtcc ctgccagctg accagaagca    2760
gcctagcctg ggggtgttc aggctttccc tccctccctc cctccctccc tccgctctcc    2820
ttttttatat tggttatttt aaggggact ctgtggggac tgagttacgg ggataccaga    2880
ggcatggggt gggaggggtc tcatgtttac atgtggagaa accctgaaca ataaaagaaa   2940
aagaccccc                                                           2948

<210> SEQ ID NO 3
<211> LENGTH: 6400
<212> TYPE: DNA
<213> ORGANISM: Bos taurus

<400> SEQUENCE: 3
ccacccggcc ctgcaactcg agctgctgcc cctggttaaa ataccccct gtcccgtcct    60 cccctccgc tccccgcgc tgccctggcg tccgggcccc agcccttccc acccagatag     120
gcgctggccc ctccccgggg actactctgc ctttgactaa tttgtcctct cgcggagttg   180
gcccagcgtc tgcggaggag ggccgaggag ataccgtgaa ttagagagat cgtcggagaa   240
ggtgcccgga gaggagggcg gagaggaagc ggggtggaag cccgaggaga aggaggagga   300
gaagggaggg gcggaggagg gcggggagga gcgctcttcc tggttgggcc ctgtcctcag   360
ttgccacccg ggaagccaga gcagggaccg cagcgacccc ccaacactcc tcccccaggt   420
aaggagggtg aggccggccc ggcgttcccc cagcttggcc tggatcccgg atgtgggct    480 gccttccccc cgggctctca gagtgcctgc gacggggcgg gggctcggga accgcaaggc   540
tccgagcccc gccccaggct gcgttcctca cggtctccag gggctgggct ggggctggc   600 gggaggggaa aggactgagg ccgagcctcc ctgatccttc aacccgtctc aggagcctgg  660 ggagggaac cccggactgc ctggacttat cagccccaa gctggcaaag gggccagtgc    720
ctaggagctt ggctagtctg gggagagagg cattcaaaga gtacttgcct cggggtctcc   780
caccttcctc gttccttgtg ctattatctc ggaccccgcc cttccccacc tgactggctg   840
accgcaggcc tgcagaccca ggacaatggg agtctgggaa cggagaggtg gtagcattgg   900
gtgagggtag ggagatgatg gccagcgcac ctagggggatg ggaagccccc tctggtggat   960
tctgggagca gagaggtatg gctgcccgcc ctaatttagt gaggaggtgg ggaaaccaca   1020
ggcttgggga gaaaggaggg cagcgggcca gagagcagtg ttagcagata ggagccccag   1080
ctctagtcct gggaaggcca gggttctgag cagggccct ctgtcccaca ggatggccga    1140
ggagttcatc actccggtgt actgcaccgg ggtgtctgca caagtgcaga agcagcgggc   1200
caaggagctg ggcctgggcc gccatgaaaa tgccatcaag tacctgggcc aggattacga   1260
gcagctgcgg gttcactgcc tgcaaagagg ggccttttc cgtgacgagg ctttccccc     1320 agtgccccag agcctgggct tcaaggagct gggccccaac tcctccaaaa cctatggcat   1380
caagtggaag cgtccacgg tgagaggggc caccctggat gggactcagt ttacctcctt    1440
cctgagtgag gagtgggaat aggacgccag gtccctagag tggggtctgg gatggctggg   1500
```

-continued

```
ctccagtttc taggaggggc tggcccagag acaggactct gggtctcttg caggagctgt    1560
tctcaaaccc ccagttcatc gtggatggag ccacccgcac ggacatctgc cagggcgcac    1620
tgggtaggcc ctgggggatc ccgagtgtgt tttgcgtagt agttccctgt gcccgttcct    1680
tcctgctccg cctcagcctc tccctcctgc aagcccgagc aggctctggc tctcagtgct    1740
ggggctggtt tgcccagatt cctgggtctt ttctgtaagt tgaggggcac cctgtccggg    1800
gagtcccagg ttctccccag tatggcactc actgggcaaa gatgggtaca gtagacctga    1860
cggggatcct tcccatccca ggggactgtt ggctcctggc tgccatcgcc tcccttaccc    1920
tcaatgacac cctcctgcac cgagtagttc acatggccaa agcttccag gatggctacg    1980 ctggcatctt ccatttccag gtgaggagcc ccacatgcac cttggacaag gagtggggcg    2040
gtgagggaga gagggtagc aggcaacgga gatgggcggg ggaccctgaa gttagggtgg    2100
cgcggggccg caccttgcag ggccagctcc ccgcaccccc ccccaccccc cagaaagtat    2160
gtgacctctt gattccatct caggtctgtc atgtgtgaga atctgtcatg tgtgaaacgg    2220
ttgggcaggt atttcagctg gcagttttcc tggctggttg tgcacactgg agaaaagaaa    2280
gtgcttagag aaaattctct gggttatgtc ctacgggaca aatccttttc ctcctcaggg    2340
tctcagtttc cctgtctgag aaatagtgtt ctgctgggga aaatcggctg tcacttgtgg    2400
tcatctacac ccttggcctc agtctccccc cgacccctc accccaact cctcctgcac    2460 tctgtcagtc tccagccact gagagccctg aggaaaagaa agactctgga taaagtttat    2520
ttaaaccagc ttttcctgat gctctttgcg cacagggccc acttttcaaa ttacactgat    2580
gaattctcag taggctcgtt ttgggaaaga acatgccca gcaaccctgg atgagaacct    2640
ctggcgccgg tgtcctctcc taccttctgg tcagggagcg ccttgcccta cttcatcctc    2700
acccgccttg gcgcatttgg cttcacttga cgggaccac agtgcggggc gaactactgt    2760
ggccaagtgc ggcaccctgcc agcgctggtc tgcaggggcg tggcctcgct gtcctttccc    2820
caccctctcc tcttactcct ccaatccgtt cctccacggc ctctgattgg cccgttcact    2880
ttctccatgg tgctgtgggc gcacctcctc ccttttgccc cattgttttg cacactcacg    2940
gcccccagtg ctgtagcaca gagtcactta tggcctggga tggcgggaag tccttccccc    3000
actgggaaac ttgcctttca aggcatcttt gaagcaagcc cgtgattgtg ggaatcctgt    3060
ccaccttgtg gttgaaggat ctggatcctg catcttcatt ccacaccaat ttacctaggt    3120
atccccatcc ccctacacac acacacaccc gcatttccat tccacatcta atttacctag    3180
gtatccccac tccctacaca cacacacacc cacacacacc ctggcctaga atggtgggga    3240 ggggaaagt ctgggtcat ggtagggcc agcagagcca gggtccaagg gctttgcaac    3300
gtctctgtac ctgaagaggc aacttggtct gtttcaaaaa tatgaacaat gctgccttac    3360
aagtgttgcc tgcctaatct tgtttagttt tcccattagg aaggcattat tgttcccttt    3420 tgtgagggg gaaacaggct cagcgaggac gacctgctca gatcctgtgt ctaggatgcg    3480
tggcctagaa tcaggtatct agtgagtggc agagctgctg aggcctgacc tcaggcctga    3540
cctcaggccc gagggatctc aaagcaggga ttcactgtgc ccctcctccc ccagctgtgg    3600
cagtttggtg agtgggtgga tgtggtggtg gatgacctgc tgcccaccaa ggacgggaag    3660
ctggtgtttt tgcactctgc ccaaggcaac gagttctgga gcgccctgct ggagaaggcc    3720
tatgccaagt gagtgggggc ccagggacag ctccaggcca cgcctgggtt gggggtcctg    3780
cttggtgcaa atggtgacc tgggccgccc acagggtgaa cggcagctac gaggccctct    3840
caggaggcag cacatctgag ggctttgagg acttcaccgg cggagtcacc gagtggtacg    3900
```

```
agctgcgcaa ggcgcccagc gacctctaca acatcatcct caaggccctg gagcgtggct   3960
ccctgctggg ctgctccatc gatgtaagtg cctcccccat cctgggacct gagtctccta   4020
gcggttcctt ctctctactc agcccagcct cagacttgcc acgggcttgg ctccagaccc   4080
tgtcctttgc ctcacaccat ccctggatcc tcagccagcc tggctcatca cctcagtcct   4140
gtcctccacc tccatgcctg gcttcctcct ggttcccaaa acctcagact tcagcatgtt   4200
ctccaacttc ctctttcctg tcatctgagg ccatgcctgt gcgctgtcca gttcacagcc   4260
tggcctcagc tcctcccgag tcccagttcc tgtgggcccc agactcccca tttgttcctt   4320
cagttgctct ctgttccccg acttatcttc agacctccct catccttgat ctcggcctcc   4380
accgccacca tcactgcatt ctccattcta accccgctgc cgcgctcttc ccagcccta    4440 cccgactcta gtctctgctc acccctcttc tctgcctccc tgagtccctc cacatgaggt   4500
cctctgagga cctcgtggct cctgggtgag gggagaggct ttgcatggct gtatgtttgt   4560
gttcacgcat gtgtgcccag ggtctggcca gctctggcca gaagcagtgt cagtggggtg   4620
cacacccccc tcaccagcag tatcattggt ggagtagcca gcagctcccc cttccaggga   4680
ctgagatggg gtcaggggtc ctgcccatca ctcccagtaa ctgtgggtgt atgcaaggga   4740
aagccaggac tcggggctca tctcctgaat ggggtggggg acagcggccg cagcccatgt   4800
gtctttctgc agatctccag cattctggac atggaggctg tcaccttcaa gaagctggtg   4860
aagggccacg cctactctgt gaccggggcc aaacaggtac tgccccaggt ggaggtcttc   4920
cccaaagggt ggttccagcc tccttgcctc tctggcctgt ggccaaggct gtgggagagg   4980
ccgactctcc ccgtgacctt cagcagcacc ttcctatctc caggggactc tcgcccaaag   5040
atggttatct tgtcccaccc tgatttactg tactttgtgt gtagagctgc ctctctcagc   5100
agtttatgcc cagacaggct tctcagctgt gcttccaacg gtgggtgctg ggtgctgagc   5160
tgggctctgt gaggatgagg tggtgggaag gggtgttaaa atgtgtgcca gaagcaggcg   5220
ctgacgtgag ctctggggaa caggtgaact accagggcca gatggtgaac ctgatccgga   5280
tgcggaaccc ctggggcgag gtggagtgga caggagcctg gagtgacggg tgagggtcca   5340
tggaggctgg ccggggaggc ctgggaagac tcttcagtgc cactggcatt tctgctgggg   5400
tctctgccat cccacagtgg actcaggctt gaacagaggg gcccatctgc gtgtgactgg   5460
gtctggggac tgccctggca aagctcaggc tgtgcgtgca ggcggctgtg cccacctacc   5520
agcatcctcg gggcgtctga gctggccctc ataagataac ccctgggact ggggtctctg   5580
gacttgccct tgtggaggcc tcctgacctg gccagggaa ggacaggccc cagggataga   5640
ggctgggcag gtcagtggcc gccagcccct ggcagtgccg ttttcctaca gctcctcgga   5700
gtggaacgsc gtggacccctt acatgcggga gcagctccgg gtcaagatgg aggatgggga   5760
gttctggtga gcagccccct cctcagtctg agtgggcacc ccagctccca accccacccc   5820
cctgaaaacc agctgtgcca tgtctcttga tgcctcgact gggcatcctg gttcactctc   5880
acctcgaccc cccaggatgt ccttccgaga cttcatgcgt gaattcaccc gcctggagat   5940
ctgcaacctg acacccgacg cgctcaagag ccagaggttc cgcaactgga acaccaccct   6000
gtacgagggc acctggcggc gggggagcac cgtgggggc tgccgcaact acccaggtga   6060
cctggggagt ggggtcctgg gccctgctgc cctggacaag acgtatcttc tctctgagcc   6120
tgtttcctca cctgtaagat agggggtagtt gtacttgttt tgcaaatttg gtttgaggat   6180
gaaaaagtgt gaattcccaa gagccacctt tgactgcctt gctggagcct gagctcaggg   6240
```

-continued

```
tgcggacaga ggagacttcc ttgctgtcca gccacctcct gtcactcctc cttccgggcc      6300
ttcctcctgg cccgctgtct ccctccttgg tccttctgtc gcctttccct ggggtccatg      6360
ggcatccttc ctctcccacc ctgccttctc ttcttaacag                            6400
```

<210> SEQ ID NO 4
<211> LENGTH: 9800
<212> TYPE: DNA
<213> ORGANISM: Bos taurus
<220> FEATURE:
<221> NAME/KEY: variation
<222> LOCATION: (4558)
<220> FEATURE:
<221> NAME/KEY: variation
<222> LOCATION: (7367)

<400> SEQUENCE: 4

```
tcactggagc cccgctgtgg gtctttttt ctctctctgc cttgtcctgt ttcccaggcc        60
ttcttcttca ggtctcagct cacaggtcac ctggaggatt ccttccctgc ccagctccag      120
cttgctctct ttgtaactgt cccattgcct aacctgactt gctcgcgctt tgcctccttc      180
tggaatgtga gctcctgagg cagggacttc gtgtgtcccc tctgcacaca tggcacttgg      240
cacacggtgg acccagtgat acttgttgaa tgaacacatg gaggagggaa ggcttgatgg      300
gaggctgctc tcctccgcct ctctgctgat ccctgcctct ctacctcctg cagccacttt      360
ctgggtgaac cccagttca agatccggct ggaggagacg gatgacccgg accccgacga      420
ctacgggggt cgcgagtcag gctgcagctt cctgctcgcc ctcatgcaga agcaccgccg      480
tcgggagcgc cgtttcggcc gtgacatgga gaccataggc ttcgctgtct acgaggtgag      540
caggcagatt gcgcggaatg cagcagagaa agcggcctcc cggccagctc tgccaggggg      600
tgccaggggg tctctggagg acttggtgac acctgccaat catggttcag ctggggccag      660
tcacacccct gaggtacaca gtcctaaacc tgaccttggg gaggcacctg ctgaggccca      720
ccaccagaac taaggcagcc aggggcctaa aattcttccc aggaggcgga tagtgagtga      780
ggaaaatgtt tagccaggag aagggaagat cctgagattc ttctccctgt cctcggaggc      840
cagcaggctg ctcttgggca gacctctggc ttagctgacg cctgggacac agacctcctg      900
gctcagtttc agaaagaagt gggcaagtgg tctgccctgg aggagtagtg agctccccat      960
ctgcgaagta tgtaagtgga tgctggccat ggaggaccct gctacatact ctgtattcgt     1020
gacagacaga cacttctgga tctccctggt cggggtaaag gacagtcaca gcctctgccc     1080
aggcccacag ccccctgaca gcaaactggt atggatgtct gatgtcccgg gactggagga     1140
ctttgcagtt ggccctacag ggggcaatcc tggagactcc agttcagagc tgaggtgcag     1200
ggcattccag ggaccaagag ggccccgcct ggggctcccc cctggggtcc ttctctggca     1260
tgaaaacagg tctgaggcaa cagcagcccc aggcccatcc ctaaccctcc tggtctcccc     1320
atcctgtcct tttcatctga agaactctgg gcccctgtgt ggcacacacc acaccccctg     1380
cccctgggcc aagcgtgtat ctctaactcc cctcatttct ctgcaggtcc ctccggaggt     1440
aggtgtggca cctgactcac ctggatttac acacccttga acacacgtgg cccgatgctg     1500
cccagaggga gcaggacagc ggcacgccca cacgtagaga gctaagacgc cacctcccct     1560
gggggctcac acagtgcccc cacccccctgc ccgctcttca gtgggcagag caaacactgt     1620
cctcctgtgt gtcagagcag gtaacaagtc aggaggctgg atttgaagct tgaccctcag     1680
ccctgcctga accacaccca cgaggctctt cctgtctgac tctttacact gaggacatct     1740
gggatgctgg ttgggaacag ggtagtgggt gggctgagtg ttctgtgccc ttgagcaagt     1800
```

```
cgcttaagct ctaagcctca tgggctccca tgagcataag tgaggagctt gtgtagaggg    1860
ccctacagtg tcttatatgg gaaacgcctg gtaaggatga taagaaagtt atttcatggt    1920
gtcatcagtc agttcagtcc ctcagtcacg ttcgactctt tgcgacccca tggactgtag    1980
catgccaggc ttccctgtcc atcaccagct cccagagctt actcagattc atgtccattg    2040
agtcggtgat gccatccaac tgtctcatcc tctgttgtgc ccttctcctc ccaccttcaa    2100
tctcttctaa tgagtcagtt cttcccatca ggtggccaaa gtattggagc ttcagcatca    2160
gttcttccaa tgaatattca ggactgattt cctttcagat ggactggttt gatctctttg    2220
cagtccaagg gactctgaag agtcttctcc aacaccacag ttcaaaagca tcaattcttt    2280
agcactcagc tgtctttatg gtccaattat cacattcata tgtgactact ggaaaaacca    2340
ttgctttgac tagatggacc tttgtcaacg aagtaatgtc tctgcttttt taataagctg    2400
tctaggtttg tcatagcttt tcttccaagg agcaagtgtc ttttaatttc atggctgcag    2460
tcaccatctg cagtgatttt ggagcccaag aaaatagtct gttactgttt ccattgtttg    2520
cccatctatt tgccatgaag tgatgggact ggatgccatg atcttagtgt tttgaaagtt    2580
gagttttaag ccagttttt cactctcatc atcaacaggc tctttagttc ctcttcactt     2640
tctgccatta gggtggtgtc atctgcatat ctgaggttgt tgatatttct ccccgcagtc    2700
ttgattccag cttgtgcttc atccagccca gagtttctca taatgtactc tgcatataag    2760
ttaaataagc agggtgacga tatacagcct tgacgtactc ctttcccaat tttgaaccag    2820
tctgttgttc gaggtccggt tctaactgtt gcttcttgac ctgcatacag atttctcagg    2880
aggttggtaa ggtggtctgg tattcccatc tcttgaagaa ttttcagtt tattgtgatc      2940 cacacagtca aaggctttgg catagtcaat aaagcagatg ttttctgga attctcttgc     3000 tttttctatg atccaacagt tgttggcaat tgatctctg gttcctgtgc cttttctaaa     3060
tccagcttga acatctggaa gttcttggtt cacgtactct tgaaacctag cttggagaat    3120
tttgagcatt actttgctag catgtgagat gagtacaatt gtgtggtagt ttgagcattc    3180
tttggcattg ccttttctttg ggattggaat gaaaactgac cttttccatt cctgtgggcca  3240 ctgctgagtt ttccaaattt gctggcatat tgagtgcagc actttcacag catcgtcttt    3300
taggatttga aatagctcag ctagaattct atcacctcca ctagctttgt tcgtagtaat    3360
acttcctaag gcccacttga ctttgaattc caggatgtct ggctctagtt gagtgatcac    3420
accattgtgg atatctgggt cattaagatc ttttttgtat agttcttctg tgtattcttg    3480
ccacctcttc ttaatatctt ctgcttctgt taggtccata ccatttctgt cctttatcga    3540
gcccatcttt gcatgaaatg tttccttggt atctctaatt ttcttcaaga gatctctagt    3600
cttccccatt ctgttgtttt cctctatttc tttgcactga tcactgagga aggctttctt    3660
atctcttctt gctattcttt ggaactctgc attcaaatgg gtatatcttt ccttttttcc    3720
tttgcctttc atttctcttc ttttcttagc tatttgtaag gcctcctcag acaaccactt    3780 tgccttttg catttctttt tcttggggat agttttgatc actgccttct gtacaatgtc     3840
acgagcctct gtccatagtt cttcaggcag tctatctatc agatctaatc ccttgaatct    3900
attagtcact tccagtgtat aatcgtaagg gatttgattt aggtcatgcc tgaatgtcta    3960
gtggttttcc cttactgtct gcattcacct ccgtggtgtc tcctcccctt gcccttgtgc    4020
agcaggcagg gcttttacac ccatttaca gatgaggaag cgagcaatgt gactcatcag     4080
ggatgggcag cctttgggtg actgaaccgt gacccagctc tctggcccct tggccagacc    4140
```

```
ctggagcctg aggtctgggt ctgggtctgg gggcaactcc gaagggtggg ctgagctgca   4200
gcccccactt tctcctcccc tcccaccagc tgatgggcca gccggccgtg catctgaagc   4260
gggacttctt cctgtccaac gcctcccggg cccggtccga gcagttcatc aacctgcggg   4320
aggtcagcac ccgcttccgc ctgccgcctg gggagtacgt ggtggtgccc tccaccttcg   4380
agcccaacaa ggaaggtgac tttgtgctgc gtttcttctc agagaagagc gcagggaccc   4440
agtgagtaga aagccctccc ctgtctcccc ctttcctccc accacaccct tgctgcccca   4500
accccgttg actggcccct ctctctcccc accctctgca gagagctgga tgaccagrtc   4560
caggccaatc tccccgacga ggtacgtgcc ctgcccccac cctgggtgca cgacggggac   4620
ccgggtgtcc tgtgtcttgg tctctagcca gcaaggcaga gccctcctg cagganagcca   4680
tacacatccc tcacttgcca agcactttac agtttgcaaa ggactttgcg atcgatagta   4740
atggcgcagg gcccctgggt tcttgctctc tgcagggtct gtgctgagct gtttacctgg   4800
atcacccggt ttcctccata acaaccgtgt caggtgctg tcaccgtctc tcctctcaga   4860
gggaaactca ggttcagaga ggttaaggaa tttacccaag gtcacgcagc agggatccag   4920
gctcacccct catcattggg ctgtatttcc acctccatat ttagaccaca agagttctag   4980
acaggaatac agtagggact gggttcccat tttacaaatg aggagagtga ggctctgaag   5040
tgaagtgaca cctagctgat gagtgctccc agccccgcct gctgctgctg gccacgcaga   5100
ggccaggctg gggcgcccct gacctgctct ccccaccttc cctctccagc aagtgctctc   5160
agaagaggag attgatgaga acttcaagtc cctcttcaga caactggcag gggaggtagg   5220
ctgggcctgg tggcgggtgt ctggggcact gaggggtttc cccagggcag gtgccatcct   5280
ccatctcccc ccaggacatg gagatcagcg tcaaggagct gcggaccatc ctcaacagga   5340
tcatcagcaa acgtgagcgt ccctgggtag ctgttctcca cccgtgtct gcctccacgc   5400
ccccagcccc cattcctcca gactccagga tctaggcttc tcccaccctg gctgaaccc   5460
aaccctcgg tctttgaggg cgggcaccct ccactgcctt tcagagtcct gctcacccg   5520
cttttcctc ttaaattcct cttgccagac cccattctct gtgcctgagc tccaggccct   5580
ggtgtgatta ggaacttagc tggggagtgg gccagtggtt aaggatccac ctttgatccc   5640
tggccaaggg gcagcaaagc ccttgcgcta caactggaga gtccatgtgc tgcaaggagg   5700
atcctgcgtg ccgcaaccaa gacccgacgc agccaaataa ataaatagat ggatatttca   5760
aaaaagaagc agcttagcta gctgagggca ccttagggcc agtgtgccag cccccttcgt   5820
cccagaaggc gggtgacagg tgacgggctt cactccccgt tgggtacaac tgaaggcagc   5880
tgccttttag ccttcccttt gccccgcct ctgacctctg acctccaacc tgtgcccatg   5940
cttttccctc agcccagagc ccctctcctg ctcttctcac ccttcgggac ctgaggcagc   6000
ccctagccct gccgtgaccc ccttccctgc atgtttctac tgcacttcct tcccttctgt   6060
ccagcaccgg tccttttttac tcacatctaa tcgtggtgtt gacgtggctg ttgggtcagc   6120
ggcttgatta ctagaatact ttaaactttt tctgatgata aaacaatcc tacgcacctc   6180
ctcagctaga ttttagatac cagcggacag caatggtgcc tccctgcccc tcttcccacc   6240
cagtgcaccc agcacggggc agtctgggga cactggtcgg gttgaggtgt tgagactggt   6300
cttctcttgca gacaaagacc tgcggaccac gggcttcagc ctggagtcct gccgcagcat   6360
ggtcaacctc atggatgtat cctcctgagc agggcccggg gttgggttgt cagcatagga   6420
agggcttggg ttgggatgtc ggcagaggaa gggctctggg tgacctgtcc caagagcagg   6480
gaaagggaca gatgtggaca ggccagttcc ttcctggcat cctccccttg actgggggga   6540
```

-continued

```
aaaccgaggc gcagggctgt gtcaagtgac gggggagggc ctcgtctaca ggtgacccta    6600
aggctggcac tcagagaaca cccctcccag cctaccccaa ttcaggcctg gctttgggca    6660
gctcctgcag cttctcccct cccctacctc gggtttctct ccacggccag tctttcctcc    6720
cctcagtgct cagtactcac tcacccagcg tctggtttac gctgtggagt tttcttctta    6780
acggccgccc agcgcgacgg caatggcaaa ctgggcctgg tggagttcaa catcctatgg    6840
aaccggatcc ggaattacct ggtaggtggt tcctgcccgc agcaccctcc cctcttctgc    6900
ggcctcagtc acagcgggcg gcgggcctcc ggctcccgga ccagctatgt gtttcccaag    6960
ccctcaccct ggcttctgcc cttctgagcc cacgtgtccc agtggctcac ccctctccc     7020
ccgaccctcg ttaaccctcc acgctgggcg gatgggaagg gctggatgct tgccgagccc    7080
tcaccctctg ccccccaccc cagtccatct tccggaagtt tgacctggac aagtcgggca    7140
gcatgagtgc ctatgaaatg cggatggcca ttgagtttgc aggtgaggcc tgagggcggg    7200
caggacctgt ggagccccca gggagatggc ccggttgct tccctgacag ctcccagggc     7260
agtggcccac ccatggggcc ttgtcagtgg gtggggtggg gttgttgatg gcagtggtgg    7320
tgaagtgata caaacagcc atctactgcc ttttctcct ggtaacygtt agcatttcct      7380
cttgtcctca ctagacttcc ctggtggctc agaggttaaa gcgtctgccc gtaatgcggg    7440
agacgtgggt tcgatccctg agttgggaag atccctgga aaggaaatg gcaacccacc     7500
ccagtacttt tgcctggaga atcccttaga cagagaagcc tgatagtcta cagtccatgg    7560
ggtcgcaaag agtcagacac aacttagcga cttcacttca ctcacttcac tttgtttcac   7620
tgcagcctgc gaggataggg tcttttatta tcccattgag cacagagaaa agtgtctcct   7680
cagagagggg aagtgactgg cctggagcca cacagcagg gagaagcgca gccagcctcc    7740
agggcctcca atgggagctg tgcagggctc accctcacag tcccacttca ggatgaggcc    7800
agggcttttcc gaacagatga aactggacct gtgggcctga tggccagctc ctgggtgggt  7860
cgttctgggt cctcaagctt tctctgggcc agcacttgcc caggactgcc tcccccatg    7920
gcggggctca ctctgcccag ccttccgtcc cccttcccgc acctcccggg gcctcacctg    7980
ctctcctggg ccaggcttca agctcaacaa gaagctgtac gagctcatta tcacccgcta   8040
ctcggagccc gacctggccg tggacttcga caacttcgtg tgctgcctgg tgcggctgga   8100
gaccatgttc cgtgagtgtc cccatgggcg ccccccttccc acgagggtct cggggaatgg  8160
agctgggggt ccacacaggc tgagtgccag gagatgagga gtatggaggg aactttggag   8220
ggggctctcg ggcagcaggg ggaggtggag ggtgaggctg gaggtggggc tggccctcga   8280
actcgtgtct caccgagccc tcctcccatc tcgtttcttg aacacacagg ttttttcaaa   8340
actctggaca ctgatctgga tggagtggtg acctttgact tgtttaaggt gggattctcc   8400
tctggtcggg tggggaagg cactcagggg cagtgggttt ttctcacccg ccccccaccc    8460
cggagggct ggagcctgca gcctcagagt cagccctgag gctggccacc tgcatcctgc    8520
acagacacag caaggatctc tggttctga gggtgggggc aggaagaccc aggcccctgg    8580
aggcctgcac aggagccggc agcctgggct cccagggta gaggaggtaa gagtggcccc    8640
ctccccagga gggtccctct ccctcctgcc cttgacagag ggaggagaca gcagcccctg   8700
agccatggag ctgggaggcg ggacttgggg cctctgccct ggctgactgc tctctatgcc   8760
ctctctgccc ggcagtggtt acagctgacc atgtttgcgt gagacggggg ctcaggcccc   8820
cttgctatgc tcctctgccc tcctcgtccg ccaagccatg ccttcctgcg acgccacacc   8880
```

```
aggccacacc agctgcaagt gccttccttg gagcaggagg cggcctcgac ctcctgtccc    8940
ctcgcctctc agccgccgtg tttcatttgc tctgggcaga gccgtggggc cctccctgcc    9000 tccaccggc ccctccggtc gccagaccag ggaggcagct ttcgctagtt cctgcctcag     9060 gatgggctc cccggggagc tgggggcccc aagcctccca catcctgacg tgtcctctct     9120
cctgccccca caggccaccc ctcccccct ccccaccta cacactttat aaccactagc      9180
tgtgcaacag tctgcagtct agacctgtgg agccccctcc cagctgggc cccctcccca     9240 ggactgggaa cgcctgttcg tgcctgtgcg gaagccaatg ctcccctctg ccccatgacc    9300
cccctagcct gtccctgcca gctgaccaga agcagcctag cctgggggt gttcaggctt     9360 tccctccctc cctccctccc tcctccgct ctccttttttt atattggtta ttttaaaggg    9420
gactctgtgg ggactgagtt acggggatac cagaggcatg gggtgggagg ggtctcatgt   9480
ttacatgtgg agaaaccctg aacaataaag aaaaagaccc cacttttgtc tctggagtat    9540
gtttctgcct aaacctgctg gcccacaagg gtaccttatc ctgcacccac ccctgccctg   9600
ccctctgtct ccttccccat cgccccagtg gctggcacct ctgcccaagt cctgggcatc   9660
tgacaggggg tggggggcgg ggatgggacc acactgctga gtcccacat ggccctgctg    9720 gtcctccatg ccccctcct ctgagccctg accccttcct tccctgcaca ttctgcaggg    9780
aacgtgaggc tctggctgag                                                9800

<210> SEQ ID NO 5
<211> LENGTH: 75
<212> TYPE: DNA
<213> ORGANISM: Bos taurus
<220> FEATURE:
<221> NAME/KEY: variation
<222> LOCATION: (18)

<400> SEQUENCE: 5
ctcctcggag tggaacgscg tggaccctta catgcgggag cagctccggg tcaagatgga    60
ggatggggag ttctg                                                     75

<210> SEQ ID NO 6
<211> LENGTH: 40
<212> TYPE: DNA
<213> ORGANISM: Bos taurus
<220> FEATURE:
<221> NAME/KEY: variation
<222> LOCATION: (17)

<400> SEQUENCE: 6
agagctggat gaccagrtcc aggccaatct ccccgacgag                          40

<210> SEQ ID NO 7
<211> LENGTH: 812
<212> TYPE: DNA
<213> ORGANISM: Bos taurus
<220> FEATURE:
<221> NAME/KEY: variation
<222> LOCATION: (185)

<400> SEQUENCE: 7
gtgaggcctg agggcgggca ggacctgtgg agcccccagg gagatggccc gggttgcttc    60
cctgacagct cccagggcag tggcccaccc atggggcctt gtcagtgggt ggggtggggt   120
tgttgatggc agtggtggtg aagtgataac aaacagccat ctactgcctt tttctcctgg   180
taacygttag catttcctct tgtcctcact agacttccct ggtggctcag aggttaaagc   240
```

```
gtctgcccgt aatgcgggag acgtgggttc gatccctgag ttgggaagat cccctggaga     300
aggaaatggc aacccacccc agtactttg cctggagaat cccttagaca gagaagcctg      360
atagtctaca gtccatgggg tcgcaaagag tcagacacaa cttagcgact tcacttcact     420
cacttcactt tgtttcactg cagcctgcga ggatagggtc ttttattatc ccattgagca     480
cagagaaaag tgtctcctca gagagggaa gtgactggcc tggagccaca cagccaggga     540
gaagcgcagc cagcctccag ggcctccaat gggagctgtg cagggctcac cctcacagtc     600
ccacttcagg atgaggccag ggctttccga acagatgaaa ctggacctgt gggcctgatg     660
gccagctcct gggtgggtcg ttctgggtcc tcaagctttc tctgggccag cacttgccca     720
ggactgcctc cccccatggc ggggctcact ctgcccagcc ttccgtcccc cttcccgcac     780
ctcccggggc ctcacctgct ctcctgggcc ag                                   812
```

<210> SEQ ID NO 8
<211> LENGTH: 18
<212> TYPE: DNA
<213> ORGANISM: Bos taurus

<400> SEQUENCE: 8

```
ctgctgcccc tggttaaa                                                    18
```

<210> SEQ ID NO 9
<211> LENGTH: 18
<212> TYPE: DNA
<213> ORGANISM: Bos taurus

<400> SEQUENCE: 9

```
ggccaagctg ggggaacg                                                    18
```

<210> SEQ ID NO 10
<211> LENGTH: 19
<212> TYPE: DNA
<213> ORGANISM: Bos taurus

<400> SEQUENCE: 10

```
gccgaggaga taccgtgaa                                                   19
```

<210> SEQ ID NO 11
<211> LENGTH: 20
<212> TYPE: DNA
<213> ORGANISM: Bos taurus

<400> SEQUENCE: 11

```
ctggcccagg tacttgatgg                                                  20
```

<210> SEQ ID NO 12
<211> LENGTH: 18
<212> TYPE: DNA
<213> ORGANISM: Bos taurus

<400> SEQUENCE: 12

```
gatccttcaa cccgtctc                                                    18
```

<210> SEQ ID NO 13
<211> LENGTH: 20
<212> TYPE: DNA
<213> ORGANISM: Bos taurus

<400> SEQUENCE: 13

```
aggtacttga tggcattttc                                                  20
```

```
<210> SEQ ID NO 14
<211> LENGTH: 20
<212> TYPE: DNA
<213> ORGANISM: Bos taurus

<400> SEQUENCE: 14
ctgatccttc aacccgtctc                                               20

<210> SEQ ID NO 15
<211> LENGTH: 20
<212> TYPE: DNA
<213> ORGANISM: Bos taurus

<400> SEQUENCE: 15
ggtgcccctc aacttacaga                                               20

<210> SEQ ID NO 16
<211> LENGTH: 20
<212> TYPE: DNA
<213> ORGANISM: Bos taurus

<400> SEQUENCE: 16
ggtagcattg ggtgagggta                                               20

<210> SEQ ID NO 17
<211> LENGTH: 20
<212> TYPE: DNA
<213> ORGANISM: Bos taurus

<400> SEQUENCE: 17
agtgccatac tggggagaac                                               20

<210> SEQ ID NO 18
<211> LENGTH: 19
<212> TYPE: DNA
<213> ORGANISM: Bos taurus

<400> SEQUENCE: 18
gttctcaaac ccccagttc                                                19

<210> SEQ ID NO 19
<211> LENGTH: 20
<212> TYPE: DNA
<213> ORGANISM: Bos taurus

<400> SEQUENCE: 19
atgtctcttt cccaaaacga                                               20

<210> SEQ ID NO 20
<211> LENGTH: 19
<212> TYPE: DNA
<213> ORGANISM: Bos taurus

<400> SEQUENCE: 20
tggctacgct ggcatcttc                                                19

<210> SEQ ID NO 21
<211> LENGTH: 18
<212> TYPE: DNA
<213> ORGANISM: Bos taurus

<400> SEQUENCE: 21
```
ttgcaaagcc cttggacc                                          18

<210> SEQ ID NO 22
<211> LENGTH: 20
<212> TYPE: DNA
<213> ORGANISM: Bos taurus

<400> SEQUENCE: 22
atggctacgc tggcatcttc                                        20

<210> SEQ ID NO 23
<211> LENGTH: 19
<212> TYPE: DNA
<213> ORGANISM: Bos taurus

<400> SEQUENCE: 23
gtgggtcccg tcaagtgaa                                         19

<210> SEQ ID NO 24
<211> LENGTH: 20
<212> TYPE: DNA
<213> ORGANISM: Bos taurus

<400> SEQUENCE: 24
acttgacggg acccacagtg                                        20

<210> SEQ ID NO 25
<211> LENGTH: 20
<212> TYPE: DNA
<213> ORGANISM: Bos taurus

<400> SEQUENCE: 25
ggaggagggg cacagtgaat                                        20

<210> SEQ ID NO 26
<211> LENGTH: 20
<212> TYPE: DNA
<213> ORGANISM: Bos taurus

<400> SEQUENCE: 26
cgcattttca ttccacatct                                        20

<210> SEQ ID NO 27
<211> LENGTH: 20
<212> TYPE: DNA
<213> ORGANISM: Bos taurus

<400> SEQUENCE: 27
accgctagga gactcaggtc                                        20

<210> SEQ ID NO 28
<211> LENGTH: 21
<212> TYPE: DNA
<213> ORGANISM: Bos taurus

<400> SEQUENCE: 28
gctgtggcag tttggtgagt g                                      21

<210> SEQ ID NO 29
<211> LENGTH: 21
<212> TYPE: DNA
<213> ORGANISM: Bos taurus

<400> SEQUENCE: 29

-continued cagggccttg aggatgatgt t                                              21

<210> SEQ ID NO 30
<211> LENGTH: 19
<212> TYPE: DNA
<213> ORGANISM: Bos taurus

<400> SEQUENCE: 30
gctgtggcag tttggtgag                                                 19

<210> SEQ ID NO 31
<211> LENGTH: 20
<212> TYPE: DNA
<213> ORGANISM: Bos taurus

<400> SEQUENCE: 31
gagaagaggg gtgagcagag                                                20

<210> SEQ ID NO 32
<211> LENGTH: 20
<212> TYPE: DNA
<213> ORGANISM: Bos taurus

<400> SEQUENCE: 32
tctgagggct ttgaggactt                                                20

<210> SEQ ID NO 33
<211> LENGTH: 20
<212> TYPE: DNA
<213> ORGANISM: Bos taurus

<400> SEQUENCE: 33
atctggccct ggtagttcac                                                20

<210> SEQ ID NO 34
<211> LENGTH: 21
<212> TYPE: DNA
<213> ORGANISM: Bos taurus

<400> SEQUENCE: 34
ccccgtgacc ttcagcagca c                                              21

<210> SEQ ID NO 35
<211> LENGTH: 24
<212> TYPE: DNA
<213> ORGANISM: Bos taurus

<400> SEQUENCE: 35
gttgcggaac ctctggctct tgag                                           24

<210> SEQ ID NO 36
<211> LENGTH: 18
<212> TYPE: DNA
<213> ORGANISM: Bos taurus

<400> SEQUENCE: 36
ggactctcgc ccaaagat                                                  18

<210> SEQ ID NO 37
<211> LENGTH: 18
<212> TYPE: DNA
<213> ORGANISM: Bos taurus

```
<400> SEQUENCE: 37
ccaggtgccc tcatacag                                                  18

<210> SEQ ID NO 38
<211> LENGTH: 19
<212> TYPE: DNA
<213> ORGANISM: Bos taurus

<400> SEQUENCE: 38
gctgtgccat gtctcttga                                                 19

<210> SEQ ID NO 39
<211> LENGTH: 20
<212> TYPE: DNA
<213> ORGANISM: Bos taurus

<400> SEQUENCE: 39
ctggacagca aggaagtctc                                                20

<210> SEQ ID NO 40
<211> LENGTH: 20
<212> TYPE: DNA
<213> ORGANISM: Bos taurus

<400> SEQUENCE: 40
cccctggctg ccttagttct                                                20

<210> SEQ ID NO 41
<211> LENGTH: 20
<212> TYPE: DNA
<213> ORGANISM: Bos taurus

<400> SEQUENCE: 41
agatcccctt tgctcactgg                                                20

<210> SEQ ID NO 42
<211> LENGTH: 20
<212> TYPE: DNA
<213> ORGANISM: Bos taurus

<400> SEQUENCE: 42
ccataggctt cgctgtctac                                                20

<210> SEQ ID NO 43
<211> LENGTH: 17
<212> TYPE: DNA
<213> ORGANISM: Bos taurus

<400> SEQUENCE: 43
ggccacgtgt gttcaag                                                   17

<210> SEQ ID NO 44
<211> LENGTH: 15
<212> TYPE: DNA
<213> ORGANISM: Bos taurus

<400> SEQUENCE: 44
tgggcccctg tgtgg                                                     15

<210> SEQ ID NO 45
<211> LENGTH: 20
<212> TYPE: DNA
<213> ORGANISM: Bos taurus
```

```
<400> SEQUENCE: 45
atgggcaaac aatggaaaca                                              20

<210> SEQ ID NO 46
<211> LENGTH: 18
<212> TYPE: DNA
<213> ORGANISM: Bos taurus

<400> SEQUENCE: 46
gcaggcaggg cttttaca                                                18

<210> SEQ ID NO 47
<211> LENGTH: 20
<212> TYPE: DNA
<213> ORGANISM: Bos taurus

<400> SEQUENCE: 47
ctctgagaag aaacgcagca                                              20

<210> SEQ ID NO 48
<211> LENGTH: 18
<212> TYPE: DNA
<213> ORGANISM: Bos taurus

<400> SEQUENCE: 48
gagcccaaca aggaaggt                                                18

<210> SEQ ID NO 49
<211> LENGTH: 20
<212> TYPE: DNA
<213> ORGANISM: Bos taurus

<400> SEQUENCE: 49
aatacagccc aatgatgagg                                              20

<210> SEQ ID NO 50
<211> LENGTH: 20
<212> TYPE: DNA
<213> ORGANISM: Bos taurus

<400> SEQUENCE: 50
ggtccgagca gttcatcaac                                              20

<210> SEQ ID NO 51
<211> LENGTH: 20
<212> TYPE: DNA
<213> ORGANISM: Bos taurus

<400> SEQUENCE: 51
acttgctgga gagggaaggt                                              20

<210> SEQ ID NO 52
<211> LENGTH: 18
<212> TYPE: DNA
<213> ORGANISM: Bos taurus

<400> SEQUENCE: 52
gtccaggcca atctcccc                                                18

<210> SEQ ID NO 53
<211> LENGTH: 20
<212> TYPE: DNA
```

<213> ORGANISM: Bos taurus

<400> SEQUENCE: 53
agctccttga cgctgatctc                                               20

<210> SEQ ID NO 54
<211> LENGTH: 21
<212> TYPE: DNA
<213> ORGANISM: Bos taurus

<400> SEQUENCE: 54
tcatcattgg gctgtatttc c                                             21

<210> SEQ ID NO 55
<211> LENGTH: 16
<212> TYPE: DNA
<213> ORGANISM: Bos taurus

<400> SEQUENCE: 55
gctgcgtcgg gtcttg                                                   16

<210> SEQ ID NO 56
<211> LENGTH: 20
<212> TYPE: DNA
<213> ORGANISM: Bos taurus

<400> SEQUENCE: 56
gacatggaga tcagcgtcaa                                               20

<210> SEQ ID NO 57
<211> LENGTH: 17
<212> TYPE: DNA
<213> ORGANISM: Bos taurus

<400> SEQUENCE: 57
gcagggaagg gggtcac                                                  17

<210> SEQ ID NO 58
<211> LENGTH: 24
<212> TYPE: DNA
<213> ORGANISM: Bos taurus

<400> SEQUENCE: 58
cctcttaaat tcctcttgcc agac                                          24

<210> SEQ ID NO 59
<211> LENGTH: 23
<212> TYPE: DNA
<213> ORGANISM: Bos taurus

<400> SEQUENCE: 59
gaaaactcca cagcgtaaac cag                                           23

<210> SEQ ID NO 60
<211> LENGTH: 20
<212> TYPE: DNA
<213> ORGANISM: Bos taurus

<400> SEQUENCE: 60
ccagcaccgg tccttttac                                                20

<210> SEQ ID NO 61
<211> LENGTH: 19

```
<212> TYPE: DNA
<213> ORGANISM: Bos taurus

<400> SEQUENCE: 61
gaggtagggg aggggagaa                                               19

<210> SEQ ID NO 62
<211> LENGTH: 18
<212> TYPE: DNA
<213> ORGANISM: Bos taurus

<400> SEQUENCE: 62
ttcagcctgg agtcctgc                                                18

<210> SEQ ID NO 63
<211> LENGTH: 18
<212> TYPE: DNA
<213> ORGANISM: Bos taurus

<400> SEQUENCE: 63
catgctgccc gacttgtc                                                18

<210> SEQ ID NO 64
<211> LENGTH: 20
<212> TYPE: DNA
<213> ORGANISM: Bos taurus

<400> SEQUENCE: 64
ctggtttacg ctgtggagtt                                              20

<210> SEQ ID NO 65
<211> LENGTH: 17
<212> TYPE: DNA
<213> ORGANISM: Bos taurus

<400> SEQUENCE: 65
cctggcctca tcctgaa                                                 17

<210> SEQ ID NO 66
<211> LENGTH: 20
<212> TYPE: DNA
<213> ORGANISM: Bos taurus

<400> SEQUENCE: 66
gcagcatgag tgcctatgaa                                              20

<210> SEQ ID NO 67
<211> LENGTH: 19
<212> TYPE: DNA
<213> ORGANISM: Bos taurus

<400> SEQUENCE: 67
caggcagcac acgaagttg                                               19

<210> SEQ ID NO 68
<211> LENGTH: 20
<212> TYPE: DNA
<213> ORGANISM: Bos taurus

<400> SEQUENCE: 68
tcaccctcac agtcccactt                                              20

<210> SEQ ID NO 69
```

<211> LENGTH: 20
<212> TYPE: DNA
<213> ORGANISM: Bos taurus

<400> SEQUENCE: 69
gggccactct tacctcctct    20

<210> SEQ ID NO 70
<211> LENGTH: 17
<212> TYPE: DNA
<213> ORGANISM: Bos taurus

<400> SEQUENCE: 70
gacctggccg tggactt    17

<210> SEQ ID NO 71
<211> LENGTH: 19
<212> TYPE: DNA
<213> ORGANISM: Bos taurus

<400> SEQUENCE: 71
gcagaggagc atagcaagg    19

<210> SEQ ID NO 72
<211> LENGTH: 20
<212> TYPE: DNA
<213> ORGANISM: Bos taurus

<400> SEQUENCE: 72
gggcagtggg tttttctcac    20

<210> SEQ ID NO 73
<211> LENGTH: 20
<212> TYPE: DNA
<213> ORGANISM: Bos taurus

<400> SEQUENCE: 73
gcctctggta tccccgtaac    20

<210> SEQ ID NO 74
<211> LENGTH: 17
<212> TYPE: DNA
<213> ORGANISM: Bos taurus

<400> SEQUENCE: 74
cctctgccct cctcgtc    17

<210> SEQ ID NO 75
<211> LENGTH: 21
<212> TYPE: DNA
<213> ORGANISM: Bos taurus

<400> SEQUENCE: 75
ctggtatccc cgtaactcag t    21

<210> SEQ ID NO 76
<211> LENGTH: 20
<212> TYPE: DNA
<213> ORGANISM: Bos taurus

<400> SEQUENCE: 76
tgaccatgtt tgcgtgagac    20

```
<210> SEQ ID NO 77
<211> LENGTH: 20
<212> TYPE: DNA
<213> ORGANISM: Bos taurus

<400> SEQUENCE: 77
atgtgggacc tcagcagtgt                                              20

<210> SEQ ID NO 78
<211> LENGTH: 30
<212> TYPE: DNA
<213> ORGANISM: Bos taurus

<400> SEQUENCE: 78
cgttggatgg agctggccct cataagataa                                   30

<210> SEQ ID NO 79
<211> LENGTH: 30
<212> TYPE: DNA
<213> ORGANISM: Bos taurus

<400> SEQUENCE: 79
gacgttggat gcccatcctc catcttgacc                                   30

<210> SEQ ID NO 80
<211> LENGTH: 15
<212> TYPE: DNA
<213> ORGANISM: Bos taurus

<400> SEQUENCE: 80
cctcggagtg gaacg                                                   15

<210> SEQ ID NO 81
<211> LENGTH: 30
<212> TYPE: DNA
<213> ORGANISM: Bos taurus

<400> SEQUENCE: 81
gacgttggat gcgagcccaa caaggaaggt                                   30

<210> SEQ ID NO 82
<211> LENGTH: 30
<212> TYPE: DNA
<213> ORGANISM: Bos taurus

<400> SEQUENCE: 82
cgttggatgg tgactttgtg ctgcgtttct                                   30

<210> SEQ ID NO 83
<211> LENGTH: 17
<212> TYPE: DNA
<213> ORGANISM: Bos taurus

<400> SEQUENCE: 83
ggggagattg gcctgga                                                 17

<210> SEQ ID NO 84
<211> LENGTH: 20
<212> TYPE: DNA
<213> ORGANISM: Bos taurus

<400> SEQUENCE: 84
gcagcatgag tgcctatgaa                                              20
```

<210> SEQ ID NO 85
<211> LENGTH: 19
<212> TYPE: DNA
<213> ORGANISM: Bos taurus

<400> SEQUENCE: 85
caggcagcac acgaagttg                                                  19

<210> SEQ ID NO 86
<211> LENGTH: 20
<212> TYPE: DNA
<213> ORGANISM: Bos taurus

<400> SEQUENCE: 86
tgcctttttc tcctggtaac                                                 20

<210> SEQ ID NO 87
<211> LENGTH: 10
<212> TYPE: DNA
<213> ORGANISM: Bos taurus

<400> SEQUENCE: 87
gtttcgatcg                                                            10

<210> SEQ ID NO 88
<211> LENGTH: 10
<212> TYPE: DNA
<213> ORGANISM: Bos taurus

<400> SEQUENCE: 88
accctcgcta                                                            10

<210> SEQ ID NO 89
<211> LENGTH: 13
<212> TYPE: DNA
<213> ORGANISM: Bos taurus
<220> FEATURE:
<221> NAME/KEY: variation
<222> LOCATION: (7)

<400> SEQUENCE: 89
cagcacrtct gag                                                        13

<210> SEQ ID NO 90
<211> LENGTH: 13
<212> TYPE: DNA
<213> ORGANISM: Bos taurus
<220> FEATURE:
<221> NAME/KEY: variation
<222> LOCATION: (7)

<400> SEQUENCE: 90
caccggygga gtc                                                        13

<210> SEQ ID NO 91
<211> LENGTH: 13
<212> TYPE: DNA
<213> ORGANISM: Bos taurus
<220> FEATURE:
<221> NAME/KEY: variation
<222> LOCATION: (7)

<400> SEQUENCE: 91
agctgcytct ctc                                                        13

```
<210> SEQ ID NO 92
<211> LENGTH: 13
<212> TYPE: DNA
<213> ORGANISM: Bos taurus
<220> FEATURE:
<221> NAME/KEY: variation
<222> LOCATION: (7)

<400> SEQUENCE: 92
gctgggytct gtg                                                          13

<210> SEQ ID NO 93
<211> LENGTH: 13
<212> TYPE: DNA
<213> ORGANISM: Bos taurus
<220> FEATURE:
<221> NAME/KEY: variation
<222> LOCATION: (7)

<400> SEQUENCE: 93
tgtgacyggg tct                                                          13

<210> SEQ ID NO 94
<211> LENGTH: 13
<212> TYPE: DNA
<213> ORGANISM: Bos taurus
<220> FEATURE:
<221> NAME/KEY: variation
<222> LOCATION: (7)

<400> SEQUENCE: 94
ggaacgscgt gga                                                          13

<210> SEQ ID NO 95
<211> LENGTH: 13
<212> TYPE: DNA
<213> ORGANISM: Bos taurus
<220> FEATURE:
<221> NAME/KEY: variation
<222> LOCATION: (7)

<400> SEQUENCE: 95
gaccagrtcc agg                                                          13

<210> SEQ ID NO 96
<211> LENGTH: 13
<212> TYPE: DNA
<213> ORGANISM: Bos taurus
<220> FEATURE:
<221> NAME/KEY: variation
<222> LOCATION: (7)

<400> SEQUENCE: 96
ggtaacygtt agc                                                          13

<210> SEQ ID NO 97
<211> LENGTH: 13
<212> TYPE: DNA
<213> ORGANISM: Bos taurus
<220> FEATURE:
<221> NAME/KEY: variation
<222> LOCATION: (7)

<400> SEQUENCE: 97
agtactyttg cct                                                          13
```

-continued

```
<210> SEQ ID NO 98
<211> LENGTH: 13
<212> TYPE: DNA
<213> ORGANISM: Bos taurus
<220> FEATURE:
<221> NAME/KEY: variation
<222> LOCATION: (7)

<400> SEQUENCE: 98
ttccgarcag atg                                                      13
```